(12) United States Patent
Li et al.

(10) Patent No.: US 7,521,560 B2
(45) Date of Patent: Apr. 21, 2009

(54) 2-SUBSTITUTED QUINOLINE COMPOUNDS AND THEIR USES

(75) Inventors: Hui Li, Millbrae, CA (US); Rajinder Singh, Belmont, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 546 days.

(21) Appl. No.: 11/171,580

(22) Filed: Jun. 29, 2005

(65) Prior Publication Data

US 2006/0040982 A1 Feb. 23, 2006

Related U.S. Application Data

(60) Provisional application No. 60/584,372, filed on Jun. 29, 2004.

(51) Int. Cl.
*C07D 215/38* (2006.01)
(52) U.S. Cl. ...................... 546/156; 546/153
(58) Field of Classification Search .............. 546/153, 546/159
See application file for complete search history.

(56) References Cited

U.S. PATENT DOCUMENTS

| 2,619,419 | A | * | 11/1952 | Jennen .................... 430/386 |
| 4,087,535 | A | | 5/1978 | Heubach |
| 4,829,072 | A | | 5/1989 | Hamprecht et al. |
| 5,296,484 | A | | 3/1994 | Dannoux et al. |
| 7,070,996 | B2 | | 7/2006 | Rossi et al. |
| 7,084,156 | B2 | * | 8/2006 | DeVita et al. ............... 514/312 |
| 2004/0067878 | A1 | | 4/2004 | Hill et al. |

FOREIGN PATENT DOCUMENTS

| DE | 10123586 | * | 11/2002 |
| EP | 0098486 | | 1/1984 |
| EP | 0254866 | | 2/1988 |
| EP | 0326328 | | 8/1989 |
| JP | 11/189586 | | 7/1999 |
| WO | WO 94/24095 | | 10/1994 |
| WO | WO 01/44274 | | 6/2001 |
| WO | WO 02/18346 A1 | | 3/2002 |
| WO | WO 0218346 | * | 3/2002 |
| WO | WO 03013523 | * | 2/2003 |
| WO | WO 03/020896 | | 3/2003 |
| WO | WO 03/068743 A1 | | 8/2003 |

OTHER PUBLICATIONS

Ahamd et al. 2003, "Palladium in quinoline synthesis" *Advances in Heterocyclic Chemistry* 84:1-30.
Alvarez et al. 1991. "Marine, nitrogen-containing heterocyclic natural products. Structures and synthesis of compounds containing quinoline and /or isoquinoline units" *Heterocycles* 32(4):759-794.
Cheng et al. 1982, "The Friedlander synthesis of quinolines" *Organic Reactions* 28:37-201.
Demo et al. 1999, *Cytometry* 36(4):340-348.
Display for Chemcats, Chemical Library, Answer 1, "4-Isoxazolecarobxylic acid, 5-methyl-3-phenyl-, 6-fluoro-2-methyl-4-quinolinyl ester", © 2004 ACS on STN, CAS Registry No. 216774-15-1, Order No. BTB 01297 (1pg.), Supplier: Ambinter.
Display for Chemcats, Chemical Library, Answer 2, "6-fluoro-2-methyl-4-quinolyl 5-methyl-3-phenylisoxazole-4-carboxylate", © 2004 ACS on STN, CAS Registry No. 216774-15-1, Order No. BTB 01297 (2pgs.), Supplier: Maybridge plc.
Kametani et al. 1989, "Recent advances on the synthesis of quinoline skeleton by [4+2] cycloaddition reaction and its application to the natural products synthesis" *Studies in Natural Products Chemistry* 3:385-398.
Makosza 2001, "Nucleophilic aromatic substitution of hydrogen as a tool for the synthesis of indole and quinoline derivatives" *Heterocycles* 54(1):455-474.
Mehn-Cohn 1993, "The synthesis of pyridines, quinolines and other related systems by the Vilsmeier and the reverse Vilsmeier method" *Heterocycles* 35(1):539-557.
Randl et al. 1992 "Recent advances in the synthesis of antibacterial quinolines" *Heterocycles* 34(11):2143-2177.
Display for Chemcats, Chemical Library, Answer 2 of 7, "4-Isoxazolecarboxylic acid, 3- (2-chlorophenyl) -5-methyl-, 8-quinolinyl ester" © 2003 ACS on STN, Registry No. 331831-09-5.
Display for Chemcats, Chemical Library, Answer 3 of 7, "4-Isoxazolecarboxylic acid, 3- (3-chlorophenyl) -5-methyl-, 8-quinolinyl ester" © 2003 ACS on STN, Registry No. 303138-53-6.
Display for Chemcats, Chemical Library, Answer 4 of 7 "4-Isoxazolecarboxylic acid, 3,5-dimethyl-, 8-quinolinyl ester" © 2003 ACS on STN, Registry No. 260443-12-7.
Display for Chemcats, Chemical Library, Answer 5 of 7 "4-Isoxazolecarboxylic acid, 5-methyl-3-phenyl-, 6-fluoro-2-methyl-4-quinolinyl ester" © 2003 ACS on STN, Registry No. 216774-15-1.
Compound © 2003 ACS "Benzamide, 2,6-diochloro-N-[3-ethyl-4-[2- [(2-hydroxyethyl)methylamino]ethyl]-8-quinolinyl]".
Compound © ACS "2H-1-Benzopyran-2-carboxamide, 3,4-dihydro-6-hydroxy-2,5,7,8-tetramethyl-N-(2-methyl-4-quinolinyl)-".
Compound © 2003 ACS "Benzoic acid, 2-[[(2-phenyl-4quinolinyl)carbonyl]amino]-, 2-[[2-nitro-4-(trifluoromethyl)phenyl]amino]-2-oxoethyl ester".
Compound © 2003 ACS "4-Quinolinecarboxamide, 2-(5-chloro-2-thienyl)-N-cyclopropyl-".
Compound © 2003 ACS "Benzoic acid, 4-[[[2-(4-ethoxyphenyl) -4-quinolinyl]carbonyl]amino]-, propyl ester".

(Continued)

*Primary Examiner*—D. Margaret Seaman
(74) *Attorney, Agent, or Firm*—Foley & Lardner LLP; James J. Diehl

(57) ABSTRACT

The present disclosure provides 2-substituted-quinoline compounds that inhibit the IgE receptor signaling cascade that leads to the release of chemical mediators, prodrugs of the compounds, intermediates and methods of synthesizing the compounds and methods of using the compounds in a variety of contexts, including in the treatment and/or prevention of diseases characterized by, caused by or associated with the release of chemical mediators via degranulation and other processes effected by activation of the IgE receptor signaling cascade.

19 Claims, 3 Drawing Sheets

OTHER PUBLICATIONS

Figure 1:
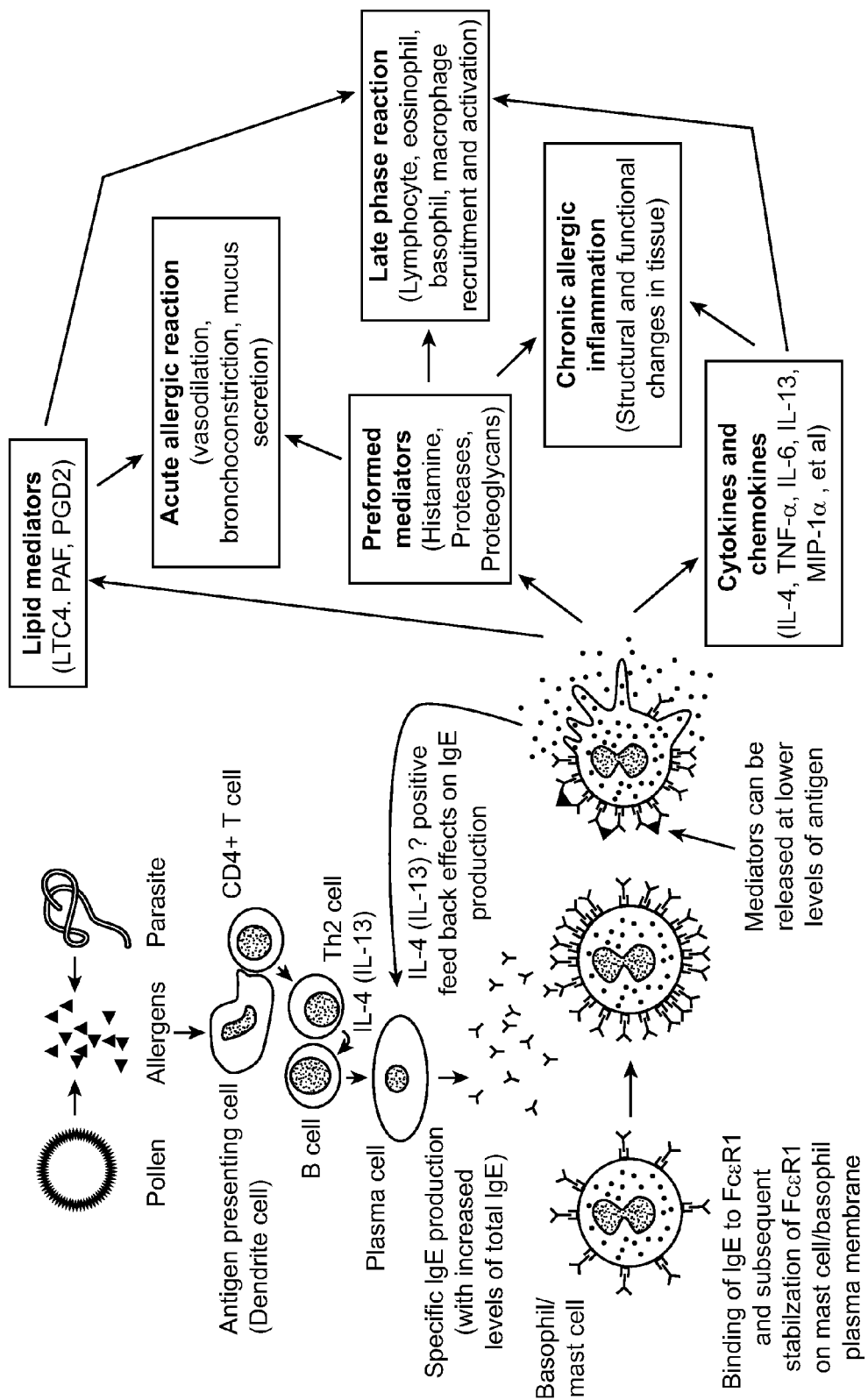

Compound © 2003 ACS "4-Quinolinecarboxamide, N-[3-(aminocarbonyl) -6- [1,1-dimethylethyl)-4,5,6,7-tetrahydrobenzo [b] thien-2-yl]-2-(3,4-dimethylphenyl)-".
Compound © 2003 ACS "4-Quinolinecarboxamide, N-(2,3-dihydro-1H-inden-5yl) -2- (3-methyl-1-piperidinyl)-".
Compound © 2003 ACS "4-Quinolinecarboxamide, 2- (2-furanyl) —N- (4-methoxyphenyl)-".
Compound © 2003 ACS "4-Quinolinecarboxamide, 6-methyl-N-(2-nitrophenyl) -2-phenyl-".
Compound © 2003 ACS "4-Quinolinecarboxamide, N-(5-methyl-3-isoxazolyl) -2-phenyl-".
Compound © 2003 ACS "Benzamide, 2,6-dochloro-N-[3-methyl-4-[(propylamino)carbonyl]amino]-8-quinolinyl]-".
Compound © 2003 ACS "Benzamide, 2,6-dichloro-N- [4-(3-ethyl-2-oxo-1-imidazolidinyl) -2,3-dimethyl-8-quinolinyl]-".
Compound © 2003 ACS "4-Quinolinecarboxamide, N- (2,3-dihydor-1,5-dimethyl-3-oxo-2-phenyl-1H-pyrazol-4-yl) -2-(4-hydroxyphenyl) -6-methyl-".
Compound © 2003 ACS "4-Quinolinecarboxamide, 2-(5-chloro-2-thienyl) -N-(4-methyl-1-piperazinyl)-".
Compound © 2003 ACS "4-Quinolinecarboxamide, 6-bromo-N-cycloheptyl-2- (4-methylphenyl)".
Compound © 2003 ACS "4-Quinolinecarboxamide, 2-(2,4-dimethylphenyl) -N-(2,5-dimethylphenyl)-".
Catalog Compound, (2003) "4-Quinolinecarboxamide, N-[3-cyano-5-methyl-4- (4-methylphenyl) -2-thienyl]-2-(5-methyl-2-furanyl)-".
Compound © 2003 ACS "4-Quinolinecarboxamide, N-(2-chloro-4-nitrophenyl) -2-phenyl-".
Compound © 2003 ACS "[6,6'-Biquinoline] -4,4'-dicaroxamide, N,N'-bis(2-chlorophenyl) -2,2' -diphenyl".
Compound © 2003 ACS "4-Quinolinecarboxamide, 2-(5-chloro-2-thienyl) -N-(2-methoxyphenyl)-".
Compound © 2003 ACS "4-Quinolinecarboxamide, N-(2-methoxyphenyl) -2-(phenylamino)-".
Compound © 2003 ACS "4-Quinolinecarboxamide, 2-(3,4-dichlorophenyl) -N-(4-methoxyphenyl)-".
Compound © 2003 ACS "1H-Pyrazole-3-carboxamide, 5-methyl-N-8-quinolinyl-1- [3-(trifluoromethyl)phenyl]-".
Compound © 2003 ACS "Benzamide, 2,6-dichloro-N-[3-chloro-5-[[2-(methylamino)ethyl]amino]-8-quinolinyl)-".
PCT International Search Report, Oct. 27, 2005.
Cusmano et al., "Rearrangement of 3-(N-Heteroarylamino)-1,2,5-Oxadiazoles: Triazolo[1,5-a] Quinolines and Triazolo[1,5-a]Pyridines," *Heterocycles.*, 1993, 36(7):1577-1587.

* cited by examiner

2-SUBSTITUTED QUINOLINE COMPOUNDS AND THEIR USES

1. FIELD

The present disclosure relates generally to 2-substituted quinoline compounds, prodrugs of the compounds, pharmaceutical compositions comprising the compounds and/or prodrugs, intermediates and synthetic methods of making the compounds and/or prodrugs and methods of using the compounds, prodrugs and/or compositions to, among other things, inhibit degranulation of mast and/or basophil cells in a variety of contexts.

2. BACKGROUND

Crosslinking of allergen to receptor bound IgE activates a signaling cascade in mast and basophil cells that results in the release of chemical mediators responsible for numerous adverse events. For example, such crosslinking leads to the release of preformed mediators of Type I (immediate) anaphylactic hypersensitivity reactions, such as histamine, from storage sites in granules via degranulation. It also leads to the synthesis and release of other mediators, including leukotrienes, prostaglandins and platelet-activating factors (PAFs), that play important roles in inflammatory reactions. Other mediators that are synthesized and released upon allergen crosslinking include cytokines and nitric oxide.

As these mediators are responsible for, or play important roles in, the manifestation of numerous adverse events, the availability of compounds capable of inhibiting the signaling cascade(s) responsible for their release and/or synthesis would be highly desirable.

3. SUMMARY

In one aspect, the present disclosure provides novel 2-substituted quinoline compounds that, among other things, inhibit degranulation of mast and/or basophil cells. The compounds generally comprise a 2-substituted quinoline "core" having the following structure and numbering convention:

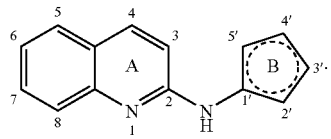

The quinolinyl moiety ("A" ring) of the compounds is substituted at one or more of the 4-, 6- and/or 8-positions. In some embodiments, when substituted at the 4-position, the substituent group is selected from a lower alkyl, a lower perhaloalkyl (e.g., trifluoromethyl), a lower alkoxy, a lower perhaloalkoxy (e.g., trifluoromethyoxy), a carboxy, a lower alkyloxycarbonyl (ester), a carboxamide (amide) and a mono- or di-loweralkyl carboxamide (substituted amide). In some embodiments, when substituted at the 6- and/or 8-position, the substituent group is an electronegative group, such as a halo, nitro, lower alkoxy or (C5-C14) aryloxy group. Other groups having chemical/physical properties similar to these exemplary groups can also be used to substitute the 4-, 6-and/or 8-positions.

The "B" ring moiety of the compounds is a five-membered saturated, unsaturated or aromatic heterocycle that includes at least two nitrogen ring atoms. Depending upon their positions within the ring and its level of saturation, the ring nitrogen atoms can be in the form of a nitrogen atom per se (i.e., N) or an NH group. The nitrogen heteroatoms can be positioned at any combination of the 2', 3', 4' and 5' ring positions (as illustrated above). In some embodiments, the "B" ring includes two nitrogen ring atoms. In some specific embodiments, the nitrogen ring atoms are positioned at the 2'- and 3'-ring positions. In other specific embodiments, the nitrogen ring atoms are positioned at the 3'-and 5'-ring positions. Specific exemplary embodiments of "B" rings containing two nitrogen ring atoms include rings of the formula

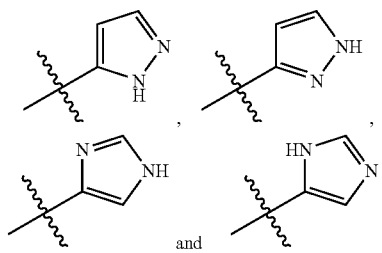

Specific examples of "B" rings containing more than two ring nitrogen atoms include triazole and tetrazole.

The "B" ring is optionally substituted at one or more available ring carbon atoms. When substituted at more than one ring carbon atom, the substituents can be the same, or they can be different. Substituents useful for substituting the ring carbon atoms of the "B" ring include, but are not limited to, electronegative groups, lower perhaloalkyl, lower alkoxy, lower perhaloalkoxy, halo, cyano, nitro, carboxyl, lower alkyloxycarbanyl, carboxamide, mono- or di-loweralkylcarboxamide, (C5-C14) aryl, 5-14 membered heteroaryl, (C6-C15) arylalkyl and 6-15 membered heteroarylalkyl. The aryl, heteroaryl, arylalkyl and/or heteroarylalkyl groups may be further substituted at one or more ring carbon atoms with the same or different substituent group. In some embodiments the substituent group(s) are, independently of one another, selected from hydroxy, lower alkoxy, carboxy, an ether, a thio ether, alkylcarbonyloxy, alkylcarbonylthioxy, alkoxycarbonyl and carbamate groups.

In some embodiments in which the "B" ring contains two nitrogen ring atoms, the substituents useful for substituting the ring carbon atoms at the 2' (or 5') ring position (according to the numbering convention illustrated above) include, but are not limited to, halo, cyano, nitro, trifluoromethyl, carboxyl, lower alkyloxycarbonyl, carboxamide and mono- or di-loweralkylcarboxamide. Subtituents useful for substituting the ring carbon atoms at the 3'- or 4'-positions include, but are not limited to, lower alkyl, halo, cyano, nitro, trifluoromethyl, aryl and heteroaryl. The aryl and heteroaryl groups may be further substituted with one or more substituent groups selected from those listed above.

The quinoline compounds may be in the form of the compounds per se, or they may be in the form of salts, hydrates, solvates and/or N-oxides, as is well-known in the art. Use of the expression "compounds," unless specifically stated otherwise, is intended to encompass all of these various different forms and/or mixtures of such forms.

In another aspect, the present disclosure provides prodrugs of the 2-substituted quinoline compounds. Such prodrugs may be active in their prodrug form, or may be inactive until converted under physiological or other conditions of use to an active drug form. In the prodrugs, one or more functional groups of the 2-substituted quinoline compounds are included in promoieties that cleave from the molecule under the conditions of use, typically by way of hydrolysis, enzymatic cleavage or some other cleavage mechanism, to yield the functional groups. For example, primary or secondary amino groups may be included in an amide promoiety that cleaves under conditions of use to generate the primary or secondary amino group. Thus, the prodrugs include special types of protecting groups, termed "progroups," masking one or more functional groups of the 2-substituted quinoline compounds that cleave under the conditions of use to yield an active 2-substituted quinoline drug compound. Functional groups within the 2-substituted quinoline compounds that may be masked with progroups for inclusion in a promoiety will be apparent to those of skill in the art. Myriad progroups suitable for masking such functional groups to yield promoieties that are cleavable under the desired conditions of use are known in the art. All of these progroups, alone or in combination, may be included in the prodrugs. Specific examples of promoieties that yield carboxyl groups that can be included in the prodrugs include, but are not limited to, esters (including silyl esters, oxamic acid esters and thioesters), amides and hydrazides.

In another aspect, the present disclosure provides compositions comprising the quinoline compounds and/or prodrugs. The compositions generally comprise one or more of the quinoline compounds and/or prodrugs described herein and a carrier, diluent and/or excipient. The nature of the carrier, diluent and/or excipient will typically depend upon the desired use for the composition. In some embodiments, the carrier, diluent and/or excipient is pharmaceutically acceptable such that the composition can be used in the therapeutic or prophylactic treatment of animals and/or humans.

The quinoline compounds described herein are potent inhibitors of mast and/or basophil cell degranulation. Thus, in still another aspect, the present disclosure provides methods of regulating, and in particular inhibiting, degranulation of mast and/or basophil cells. The method generally comprises contacting a mast and/or basophil cell with an amount of a quinoline compound or prodrug described herein, or an acceptable salt, hydrate, solvate, N-oxide and/or composition thereof, effective to regulate or inhibit degranulation of the cell. The method may be practiced in in vitro contexts or in in vivo contexts as a therapeutic approach towards the treatment or prevention of diseases characterized by, caused by or associated with mast and/or basophil cell degranulation.

While not intending to be bound by any theory of operation, it is believed that the quinoline compounds described herein exert their inhibitory effect by blocking the IgE receptor signaling cascade initiated when the IgE receptor-bound IgE is cross-linked by antigen. Thus, the present disclosure also provides methods of regulating, and in particular inhibiting, the IgE receptor (also known as FcεR1) signaling cascade that leads to mast and/or basophil cell degranulation (IgE receptor-mediated degranulation). The methods also permit the regulation of, and in particular the inhibition of, downstream processes that result as a consequence of activating the IgE receptor signaling cascade. Such downstream processes include, but are not limited to, IgE-induced degranulation, cytokine production and/or release and/or the production and/or release of lipid mediators such as leukotrienes and prostaglandins. The method generally involves contacting a mast and/or basophil cell with an amount of a quinoline compound or prodrug described herein, or an acceptable salt, hydrate, solvate, N-oxide and/or composition thereof, effective to regulate or inhibit the IgE receptor signaling cascade and/or a downstream process effected by the activation of this signaling cascade. The method may be practiced in in vitro contexts or in in vivo contexts as a therapeutic approach towards the treatment or prevention of diseases characterized by, caused by or associated with the IgE receptor signaling cascade, such as diseases effected by the release of granule specific chemical mediators upon degranulation, the release and/or synthesis of cytokines and/or the release and/or synthesis of lipid mediators such as leukotrienes and prostaglandins.

In yet another aspect, the present disclosure provides methods of treating and/or preventing diseases characterized by, caused by or associated with the release of chemical mediators as a consequence of activating the IgE receptor signaling cascade. The methods may be practiced in animals in veterinary contexts or in humans. The methods generally involve administering to an animal subject or human an amount of a quinoline compound or prodrug or an acceptable salt, hydrate, solvate, N-oxide and/or composition thereof, effective to treat or prevent the disease. As discussed previously, activation of the IgE receptor signaling cascade leads to the release and/or synthesis of a variety of chemical substances that are pharmacological mediators of a wide variety of diseases. Any of these diseases may be treated or prevented according to the methods described herein.

For example, in mast cells and basophil cells, activation of the IgE receptor signaling cascade leads to the immediate (i.e., within 1-3 min. of IgE receptor activation) release of preformed mediators of atopic and/or Type I hypersensitivity reactions (e.g., histamine, proteases such as tryptase, etc.) via the degranulation process. Such atopic or Type I hypersensitivity reactions include, but are not limited to, anaphylactic reactions to environmental and other allergens (e.g., pollens, insect and/or animal venoms, foods, drugs, etc.), hay fever, allergic conjunctivitis, allergic rhinitis, allergic asthma, atopic dermatitis, eczema, urticaria and certain gastrointestinal disorders.

The immediate release of the preformed mediators via degranulation is followed by the release and/or synthesis of a variety of other chemical mediators, including, among other things, platelet activating factor (PAF), prostaglandins and leukotrienes (e.g., LTC4), and the de novo synthesis and release of cytokines such as TNFα, IL-4, IL-5, IL-6, IL-13, etc. The first of these two processes occurs approximately 3-30 min. following IgE receptor activation; the latter approximately 30 min.-7 hrs. following receptor activation. These "late stage" mediators are thought to be in part responsible for the chronic symptoms of the above-listed atopic and Type I hypersensitivity reactions, and in addition are chemical mediators of rheumatoid arthritis, inflammation and inflammatory diseases (e.g., inflammatory bowel disease, ulcerative colitis, Crohn's disease, idiopathic inflammatory bowel disease, irritable bowel, spastic colon, etc.), low grade scarring (e.g., scleroderma, increased fibrosis, keloids, post-surgical scars, pulmonary fibrosis, vascular spasms, migraine, repurfusion injury and post myocardial infarction), certain autoimmune diseases (e.g., lupus, insulin-dependent diabetes, rheumatoid arthritis, multiple sclerosis, etc.) and sicca complex or syndrome. All of these diseases may be treated or prevented according to the methods described herein.

Additional diseases which can be treated or prevented according to the methods described herein, include diseases associated with basophil cell and/or mast cell pathology. Examples of such diseases include, but are not limited to, diseases of the skin such as scleroderma, cardiac diseases such as post myocardial infarction, pulmonary diseases such as pulmonary muscle changes or remodeling and chronic obstructive pulmonary disease (COPD) and diseases of the gut such as inflammatory bowel syndrome (spastic colon).

4. BRIEF DESCRIPTION OF THE FIGURES

Figure 2:
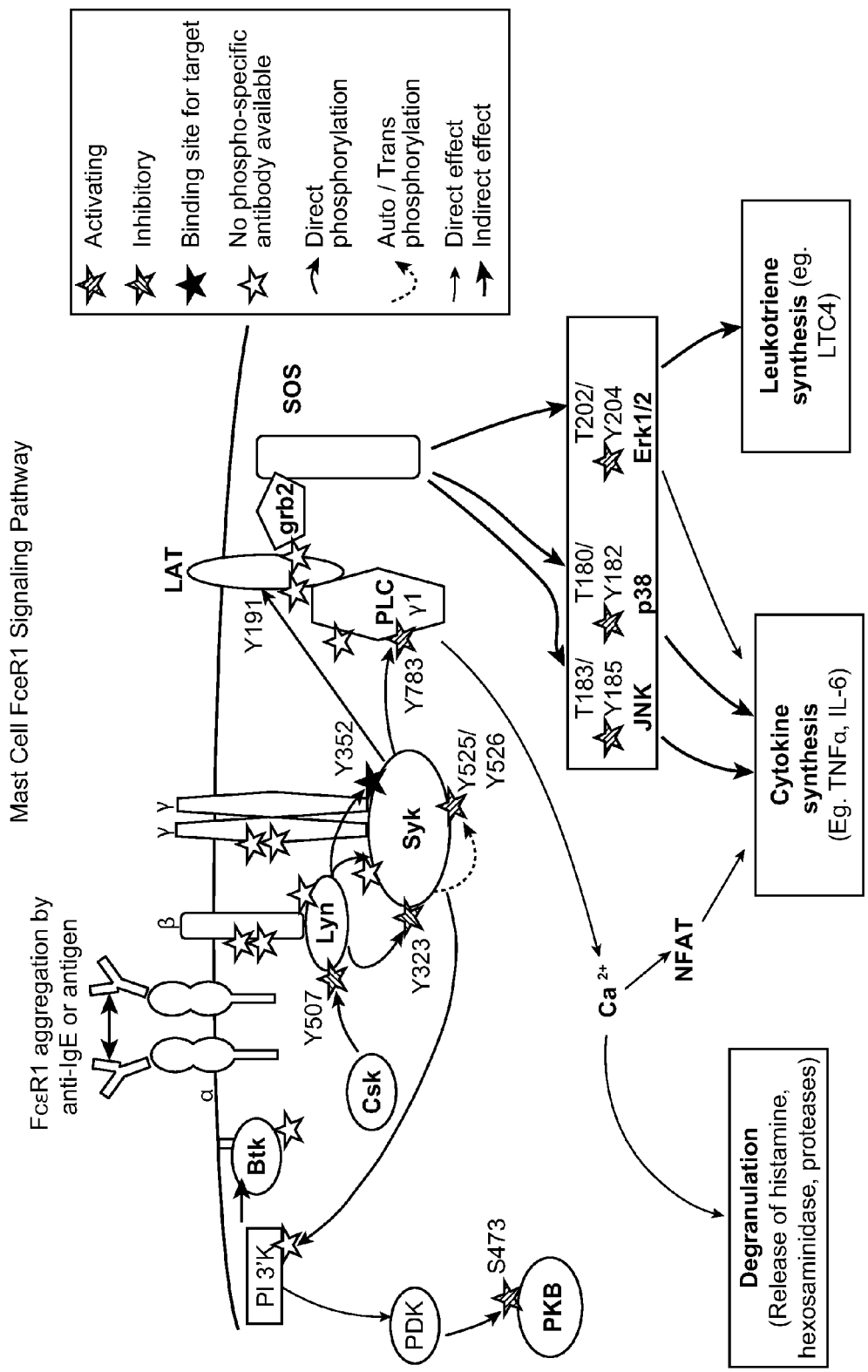
Figure 3:
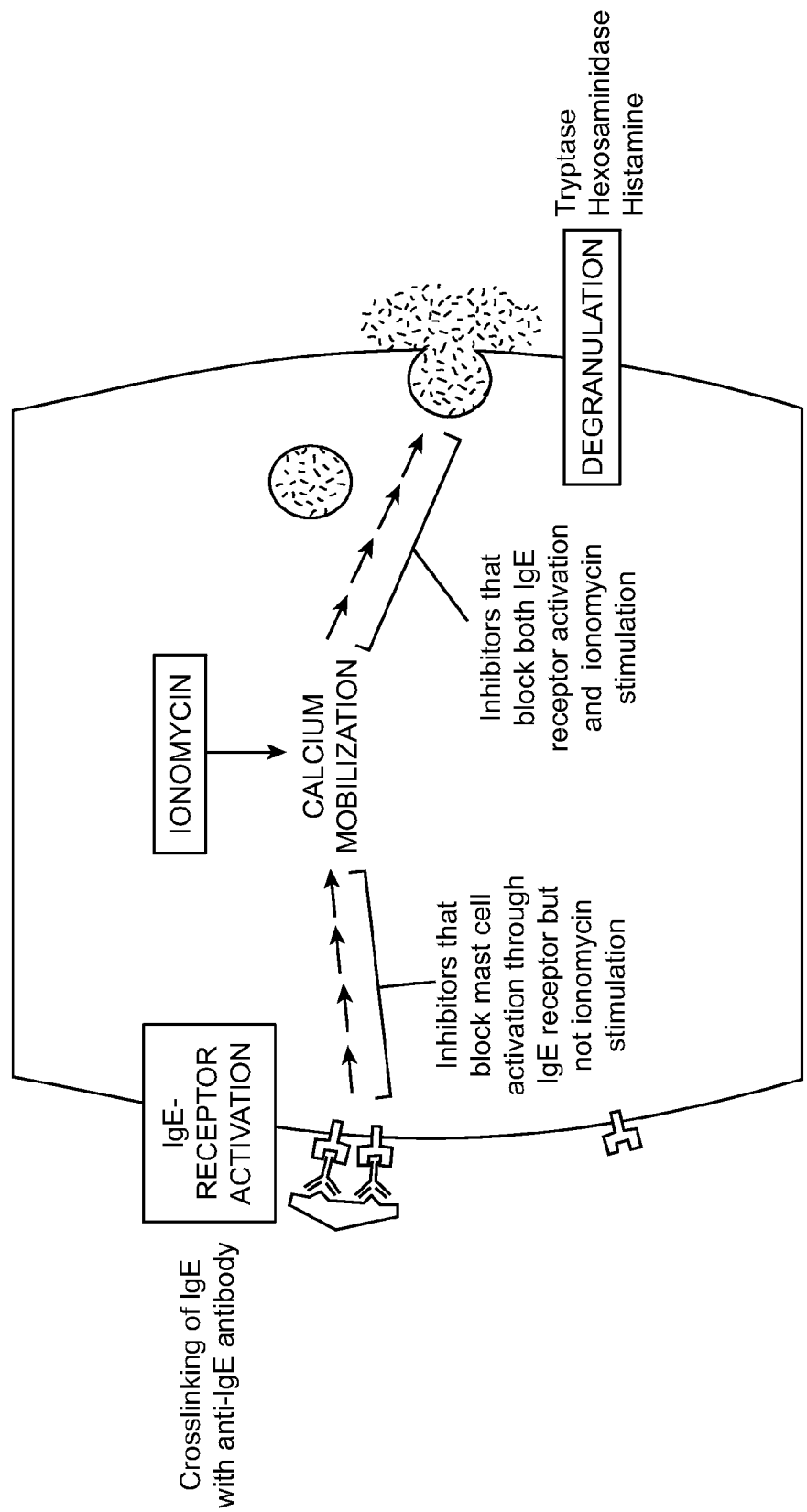

FIG. 1 provides a cartoon illustrating allergen-induced production of IgE and consequent release of preformed and other chemical mediators from mast cells;

FIG. 2 provides a cartoon illustrating the FCϵR1 (IgE receptor) signal transduction cascade leading to degranulation of mast and/or basophil cells; and FIG. 3 provides a cartoon illustrating the putative points of action of compounds that selectively inhibit upstream IgE receptor-mediated (IgE-induced) degranulation and compounds that inhibit both IgE-induced and ionomycin-induced degranulation.

5. DETAILED DESCRIPTION

5.1 Definitions

As used herein, the following terms are intended to have the following meanings:

"Alkyl," by itself or as part of another substituent, refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. "Lower alkyl" refers to an alkyl group containing from one to six carbon atoms. In preferred embodiments, the alkyl groups are lower alkanyl groups.

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent, refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy," by itself or as part of another substituent, refers to a radical of the formula —OR, where R is an alkyl group as defined herein. Representative examples alkoxy groups include, but are not limited to, methoxy, ethoxy, propoxy, isopropoxy, butoxy, tert-butoxy, cyclopropyloxy, cyclopentyloxy, cyclohexyloxy and the like.

"Alkoxycarbonyl," by itself or as part of another substituent, refers to a radical of the formula —C(O)-alkoxy, where alkoxy is as defined herein.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group contains from 6 to 20 carbon atoms (C6-C20 aryl), more preferably from 6 to 15 carbon atoms (C6-C15 aryl) and even more preferably from 6 to 10 carbon atoms (C6-C10 aryl).

"Arylalkyl," by itself or as part of another substituent, refers to an acyclic alkyl group in which one of the hydrogen atoms bonded to a carbon atom, typically a terminal or sp3 carbon atom, is replaced with an aryl group, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is (C6-C30) arylalkyl, e.g., the alkanyl, alkenyl or alkynyl moiety of the arylalkyl group is (C1-C10) alkyl and the aryl moiety is (C6-C20) aryl, more preferably, an arylalkyl group is (C6-C20) arylalkyl, e.g., the alkanyl, alkenyl or alkynyl moiety of the arylalkyl group is (C1-C8) alkyl and the aryl moiety is (C6-C12) aryl, and even more preferably, an arylalkyl group is (C6-C15) arylalkyl, e.g., the alkanyl, alkenyl or alkynyl moiety of the arylalkyl group is (C1-C5) alkyl and the aryl moiety is (C6-C 10) aryl.

"Carboxamide," by itself or as part of another substituent, refers to a radical of the formula —C(O)NR'R", where R' and R" are each, independently of one another, selected from the group consisting of hydrogen, alkyl and cycloalkyl as defined herein, or alternatively, R' and R" taken together with the nitrogen atom to which they are bonded form a 4-, 5-, 6-, 7- or 8-membered cycloheteroalkyl ring as defined herein, which may optionally include from 1 to 4 of the same or different additional heteroatoms selected from the group consisting of O, S and N.

"Halogen" or "Halo," by themselves or as part of another substituent, refer to a fluoro, chloro, bromo or iodo radical.

"Heteroaryl," by itself or as part of another substituent, refers to a monovalent heteroaromatic radical derived by the removal of one hydrogen atom from a single atom of a parent heteroaromatic ring, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group contains from 5 to 20 ring atoms (5-20 membered heteroaryl), more preferably from 5 to 10 ring atoms (5-10 membered heteroaryl). Preferred heteroaryl groups are those derived from furan, thiophene, pyrrole, benzothiophene, benzofuran, benzimidazole, indole, pyridine, pyrazole, quinoline, imidazole, oxazole, isoxazole and pyrazine.

"Heterocyclic Ring" (or "Heterocycle"), by itself or as part of another substituent, refers to a saturated, unsaturated or aromatic ring system including from one to (n-1), typically (n-2), ring heteroatoms selected from the group consisting of O, S and N, where n is the total number of ring atoms. When the ring heteroatoms are all of the same type, the heterocyclic ring is referred to as "oxygen-containing," "nitrogen-containing" or "sulfur-containing," depending upon the identities of the ring heteroatoms. Heterocyclic rings containing more than one type of ring heteroatoms are referred to as "mixed heterocyclic rings." Depending upon this position(s) within the heterocyclic ring and the degree of ring saturation, nitrogen heteroatoms can be included in the ring as the atom per se (e.g., N) or in the form of an NH group. Nitrogen and/or sulfur ring heteroatoms may, independently of one another, be included in the ring in the form of oxides or other oxidized forms.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutically acceptable salt" refers to a salt of a compound described herein that which is made with counter ions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al., 1977, J. Pharm. Sci. 66:1-19).

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, 3rd Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (e.g., methyl and ethyl esters, acetate or propionate groups or glycol esters) or alkylated such as benzyl and trityl ethers, as well as alkyl ethers, tetrahydropyranyl ethers, trialkylsilyl ethers (e.g., TMS or TIPPS groups) and allyl ethers.

"Prodrug" refers to a derivative of an active compound (drug) that undergoes a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to reveal the functional group, and hence the active drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in active compounds to yield prodrugs are well-known in the art. For example, a hydroxyl functional group may be masked as a sulfonate, ester or carbonate promoiety, which may be hydrolyzed in vitro to provide the hydroxyl group. An amino functional group may be masked as an amide, imine, phosphinyl, phosphonyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to reveal the functional group under the specified conditions of use. As a specific example, an amide promoiety of the formula —NH—C(O)CH₃ comprises the progroup —C(O)CH₃.

"FcεR1" or "IgE Receptor" refers to the high affinity receptor for the Fc region of IgE found on mast and basophil cells (as well as other cells) that anchors monomeric IgE to the cell surface. The FcεR1 or IgE receptor comprises one alpha, one beta and two gamma chains.

"IgE-Induced Degranulation" or "IgE Receptor-Mediated Degranulation" refers to degranulation that proceeds via the IgE receptor signal transduction cascade initiated by crosslinking of FcεFR1-bound IgE. The crosslinking may be induced by an IgE-specific allergen or other multivalent binding agent, such as an anti-IgE antibody. Referring to FIG. 2, the IgE receptor signaling cascade leading to degranulation may be broken into two stages: upstream and downstream. The upstream stage includes all of the processes that occur prior to calcium ion mobilization (illustrated as "Ca²⁺" in FIG. 2). The downstream stage includes calcium ion mobilization and all processes downstream thereof. Compounds that inhibit IgE-induced degranulation may act at any point along the IgE receptor signal transduction cascade. Compounds that selectively inhibit upstream IgE-induced degranulation act to inhibit that portion of the IgE receptor signaling cascade upstream of the point at which calcium ion mobilization is induced. In cell-based assays, compounds that selectively inhibit upstream IgE-induced degranulation inhibit degranulation of mast or basophil cells that are activated or stimulated with an IgE-specific allergen or binding agent (such as an anti-IgE antibody) but do not appreciably inhibit degranulation of mast or basophil cells that are activated or stimulated with degranulating agents that bypass the IgE receptor signaling pathway, such as, for example the calcium ionophores ionomycin and A23187.

"Ionophore-Induced Degranulation" or "Ionophore-Mediated Degranulation" refers to degranulation of a mast or basophil cell that occurs upon exposure to a calcium ionophore such as, for example, ionomycin or A23187.

5.2 The Quinoline Compounds

As discussed in the Summary section, the quinoline compounds generally comprise a quinolinyl ring substituted at the 2-position with a 5-membered nitrogen-containing heterocyclic ring. In some embodiments, the heterocyclic ring contains two ring nitrogen atoms and is linked at a ring carbon atom to the 2-position of the quinolinyl ring via an —NH— bridge. The quinolinyl ring is substituted at one or more of the 4-, 6- or 8-positions. Substituent groups useful for substituting the 4-position include, but are not limited to lower alkyl, lower perhaloalkyl (e.g., trifluoromethyl), lower alkoxy, lower perhaloalkoxy (e.g., trifluoromethoxy), —C(O)OR$^a$ and —C(O)NR$^a$R$^a$, where each R$^a$ is, independently of the others, selected from hydrogen and lower alkyl. Substituent groups useful for substituting the 6- and/or 8-positions include, but are not limited to, electro-negative groups, halo, nitro, lower alkoxy and (C5-C14) aryloxy. In some embodiments, the quinolinyl group is mono-substituted at the 4-, 6- or 8-position.

The nitrogen-containing heterocyclic ring can be saturated, unsaturated or aromatic in character and is optionally substituted at one or both of the available ring carbon atoms. Substituent groups suitable for substituting the available ring carbon atoms include, but are not limited to, lower alkyl, lower perhaloalkyl (e.g., trifluoromethyl), lower alkoxy, lower perhaloalkoxy (e.g., trifluoromethoxy), (C6-C10) aryl, 5-10 membered heteroaryl, lower alkoxyphenyl, para-loweralkoxyphenyl, halo, cyano, nitro, —C(O)OR$^a$ and —C(O)NR$^a$R$^a$, where each R$^a$ is, independently of the others, as defined above.

In some embodiments, the two ring nitrogen atoms are positioned adjacent to one another. In other embodiments, the two ring nitrogen atoms are spaced apart from one another by an intervening ring carbon atom. In still other embodiments, the nitrogen-containing heterocyclic ring is selected from

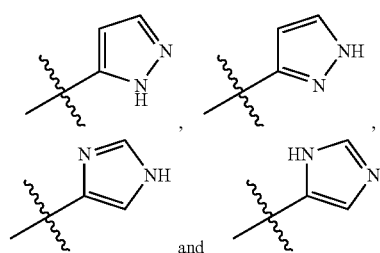

In a specific embodiment, the quinoline compounds are 2-substituted quinoline compounds according to structural formulae (I)-(IV):

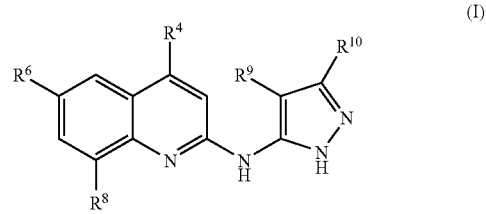

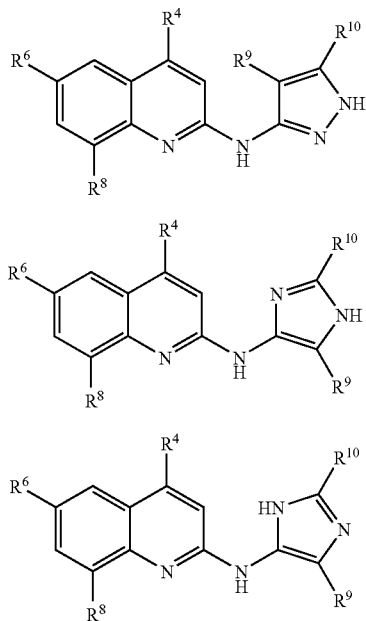

including the salts, solvates, hydrates and N-oxides thereof, wherein:

$R^4$ is selected from hydrogen, lower alkyl, methyl, —C(O)NR$^a$R$^a$ and —C(O)NHR$^a$;

$R^6$ is selected from hydrogen, halo and chloro;

$R^8$ is selected from hydrogen, halo and chloro;

$R^9$ is selected from hydrogen, halo, bromo, cyano, —C(O)OR$^a$, —C(O)NR$^a$R$^a$ and —C(O)NH$_2$;

$R^{10}$ is selected from hydrogen, lower alkyl, lower branched alkyl, t-butyl, phenyl, para-loweralkoxyphenyl, para-methoxyphenyl, 5-membered heteraryl and thienyl; and $R^a$ is as previously defined, with the proviso that at least one of $R^4$, $R^6$ and $R^8$ is other than hydrogen.

In some embodiments of the compounds of structural formulae (I)-(IV), $R^4$ is hydrogen, one of $R^6$ or $R^8$ chloro and the other one of $R^6$ or $R^8$ is hydrogen. In other embodiments, $R^4$ is methyl or —C(O)NHMe and $R^6$ and $R^8$ are each hydrogen.

In some embodiments of the compounds of structural formulae (I)-(IV), $R^9$ is hydrogen and $R^{10}$ is other than hydrogen. In other embodiments, $R^{10}$ is hydrogen and $R^9$ is other than hydrogen. In still other embodiments, both of $R^9$ and $R^{10}$ are other than hydrogen. In yet other embodiments, $R^9$ and $R^{10}$ are each hydrogen.

Exemplary embodiments of compounds according to structural formulae (I)-(IV) are illustrated in TABLE 1, infra.

TABLE 1

| Cmpd. No. | Type | $R^4$ | $R^6$ | $R^8$ | $R^9$ | $R^{10}$ | IC$_{50}$ |
|---|---|---|---|---|---|---|---|
| 1 | I | H | Cl | H | H | phenyl | +++ |
| 2 | II | H | H | Cl | Br | phenyl | +++ |
| 3 | II | H | Cl | H | Br | phenyl | +++ |
| 4 | III | H | Cl | H | —C(O)NH$_2$ | H | +++ |

TABLE 1-continued
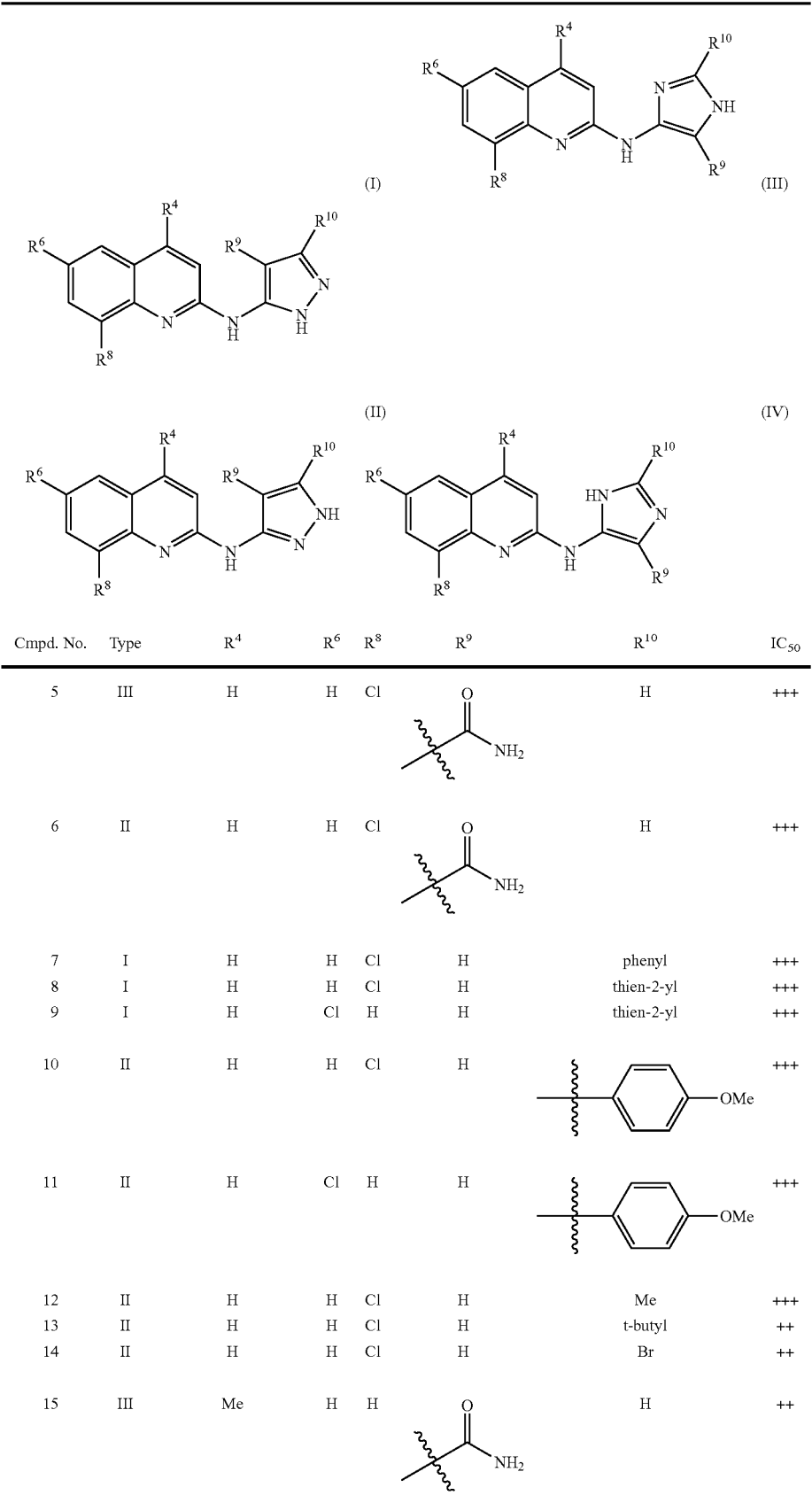
| Cmpd. No. | Type | R⁴ | R⁶ | R⁸ | R⁹ | R¹⁰ | IC$_{50}$ |
|---|---|---|---|---|---|---|---|
| 5 | III | H | H | Cl | ⟜C(Me)(—)C(O)NH₂ | H | +++ |
| 6 | II | H | H | Cl | ⟜C(Me)(—)C(O)NH₂ | H | +++ |
| 7 | I | H | H | Cl | H | phenyl | +++ |
| 8 | I | H | H | Cl | H | thien-2-yl | +++ |
| 9 | I | H | Cl | H | H | thien-2-yl | +++ |
| 10 | II | H | H | Cl | H | 4-MeO-phenyl | +++ |
| 11 | II | H | Cl | H | H | 4-MeO-phenyl | +++ |
| 12 | II | H | H | Cl | H | Me | +++ |
| 13 | II | H | H | Cl | H | t-butyl | ++ |
| 14 | II | H | H | Cl | H | Br | ++ |
| 15 | III | Me | H | H | ⟜C(Me)(—)C(O)NH₂ | H | ++ |

TABLE 1-continued
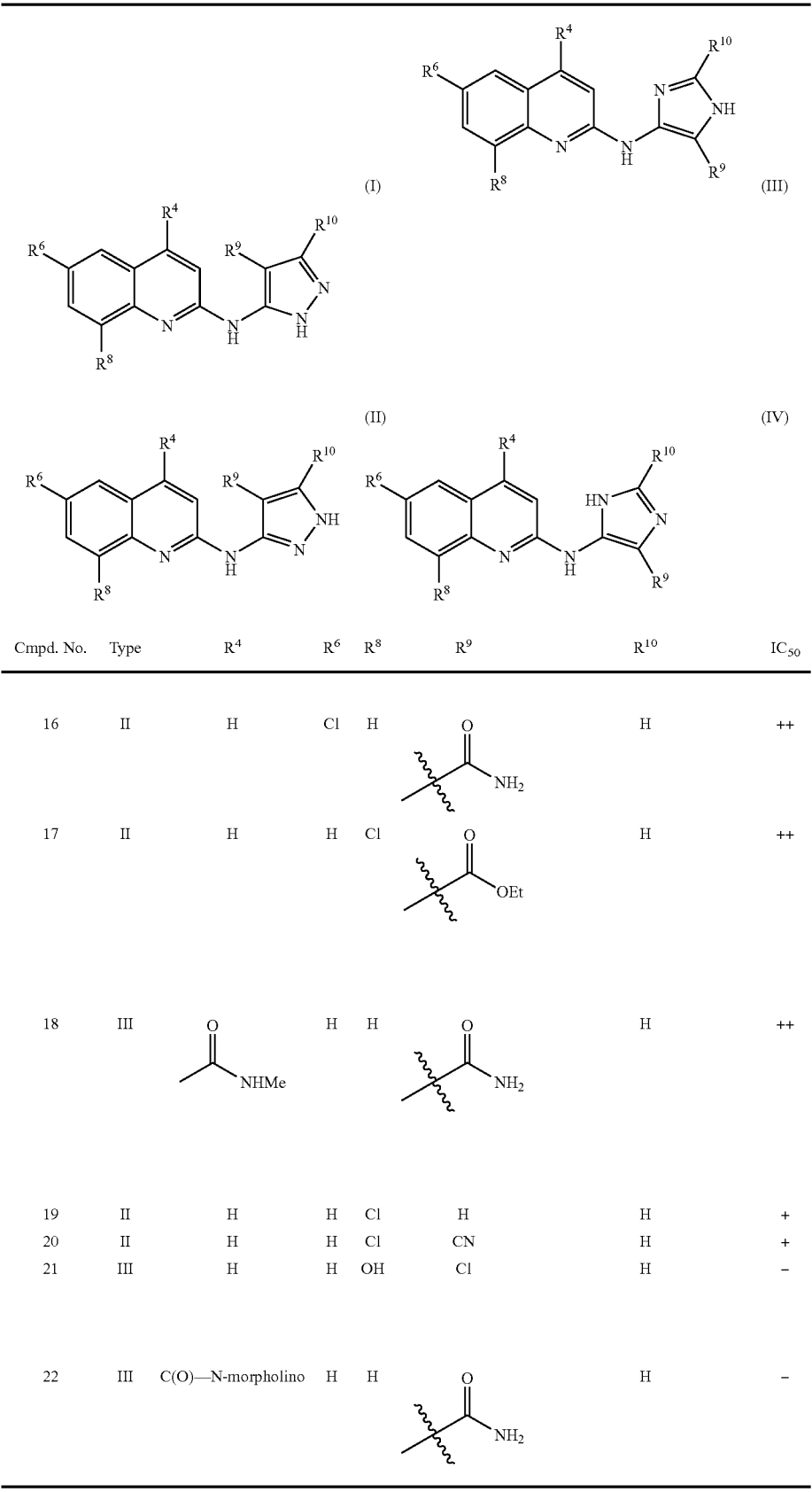
| Cmpd. No. | Type | R⁴ | R⁶ | R⁸ | R⁹ | R¹⁰ | IC₅₀ |
|---|---|---|---|---|---|---|---|
| 16 | II | H | Cl | H | -C(CH₃)(C(O)NH₂)- | H | ++ |
| 17 | II | H | H | Cl | -C(CH₃)(C(O)OEt)- | H | ++ |
| 18 | III | C(O)NHMe | H | H | -C(CH₃)(C(O)NH₂)- | H | ++ |
| 19 | II | H | H | Cl | H | H | + |
| 20 | II | H | H | Cl | CN | H | + |
| 21 | III | H | H | OH | Cl | H | − |
| 22 | III | C(O)—N-morpholino | H | H | -C(CH₃)(C(O)NH₂)- | H | − |

Those of skill in the art will appreciate that the quinoline compounds described herein may include functional groups that can be masked with progroups to create prodrugs. Such prodrugs are usually, but need not be, pharmacologically inactive until converted into their active drug form. Indeed, some of the active quinoline compounds described in TABLE 1, include promoieties that are hydrolyzable or otherwise cleavable under conditions of use. For example, ester groups commonly undergo acid-catalyzed hydrolysis to yield the parent carboxylic acid when exposed to the acidic conditions of the stomach. Thus, when administered to a subject orally, quinolines that include ester moieties may be considered prodrugs of their corresponding carboxylic acid, regardless of whether the ester form is pharmacologically active. As another example, substituted amide groups such as mono- and di-alkyl amides can oftentimes undergo dealkylation under physiological conditions. Thus, when administered to a subject, quinolines that include substituted amide groups may be considered prodrugs of their corresponding unsubstituted amides. Referring to TABLE 1, as a specific example, ester-containing quinoline 17 is active in its ester "prodrug" form. As another specific example, methylamide-containing quinoline 18 is active in its substituted amide "prodrug" form.

In one illustrative embodiment, the prodrugs are compounds according to structural formulae (I)-(IV) in which $R^a$ may be, in addition to its previously-defined alternatives, a progroup. In some embodiments, the progroup is —$CHR^e$—O—$C(O)R^e$, where each $R^e$ is, independently of the other, hydrogen or lower alkyl.

Those of skill in the art will appreciate that many of the compounds and prodrugs described herein, as well as the various exemplary compound species specifically described and/or illustrated herein, may exhibit the phenomena of tautomerism, conformational isomerism, geometric isomerism and/or optical isomerism. For example, the compounds and prodrugs may include one or more chiral centers and/or double bonds and as a consequence may exist as stereoisomers, such as double-bond isomers (i.e., geometric isomers), enantiomers and diasteromers and mixtures thereof, such as racemic mixtures. As another example, the compounds and prodrugs may exist in several tautomeric forms, including enol forms, keto forms and mixtures thereof. As the various compound names, formulae and compound drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds or prodrugs having one or more of the utilities described herein, as well as mixtures of these various different isomeric forms.

Depending upon the nature of the various substituents, the quinoline compounds and prodrugs may be in the form of salts. Such salts include salts suitable for pharmaceutical uses ("pharmaceutically-acceptable salts"), salts suitable for veterinary uses, etc. Such salts may be derived from acids or bases, as is well-known in the art.

In some embodiments, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary-butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, etc.).

The quinoline compounds and prodrugs, as well as the salts thereof, may also be in the form of hydrates, solvates and N-oxides, as are well-known in the art.

5.3 Methods of Synthesis

The quinoline compounds and prodrugs may be synthesized via a variety of different synthetic routes using commercially available starting materials and/or starting materials prepared by conventional synthetic methods. Suitable exemplary methods that may be adapted to synthesize the quinoline compounds and prodrugs are found in Cheng et al., 1982, "The Friedlander synthesis of quinolines," Organic Reactions 28:37-201; Kametani et al., 1989, "Recent advances on the synthesis of quinoline skeleton by [4+2] cycloaddition reaction and its application to the natural products synthesis," Studies in Natural Products Chemistry 3:385-398; Alvarez et al., 1991, "Marine, nitrogen-containing heterocyclic natural products. Structures and syntheses of compounds containing quinoline and/or isoquinoline units," Heterocycles 32 (4):759-794; Radl et al., 1992, "Recent advances in the synthesis of antibacterial quinolines," Heterocycles 34 (11):2143-2177; Mehn-Cohn, 1993, "The synthesis of pyridines, quinolines and other related systems by the Vilsmeier and the reverse Vilsmeier method," Heterocycles 35 (1):539-557; Makosza et al., 2001, "Nucleophilic aromatic substitution of hydrogen as a tool for the synthesis of indole and quinoline derivatives," Heterocycles 54(1):445-474; and Ahmad et al., 2003, "Palladium in quinoline synthesis," Advances in Heterocyclic Chemistry 84:1-30, the teachings of which are incorporated herein by reference. Specific examples describing the synthesis of representative quinoline compounds are provided in the Examples section. All of the quinoline compounds and prodrugs described herein may be prepared by routine adaptation of these methods.

An exemplary synthetic route is illustrated in Scheme (I), below:

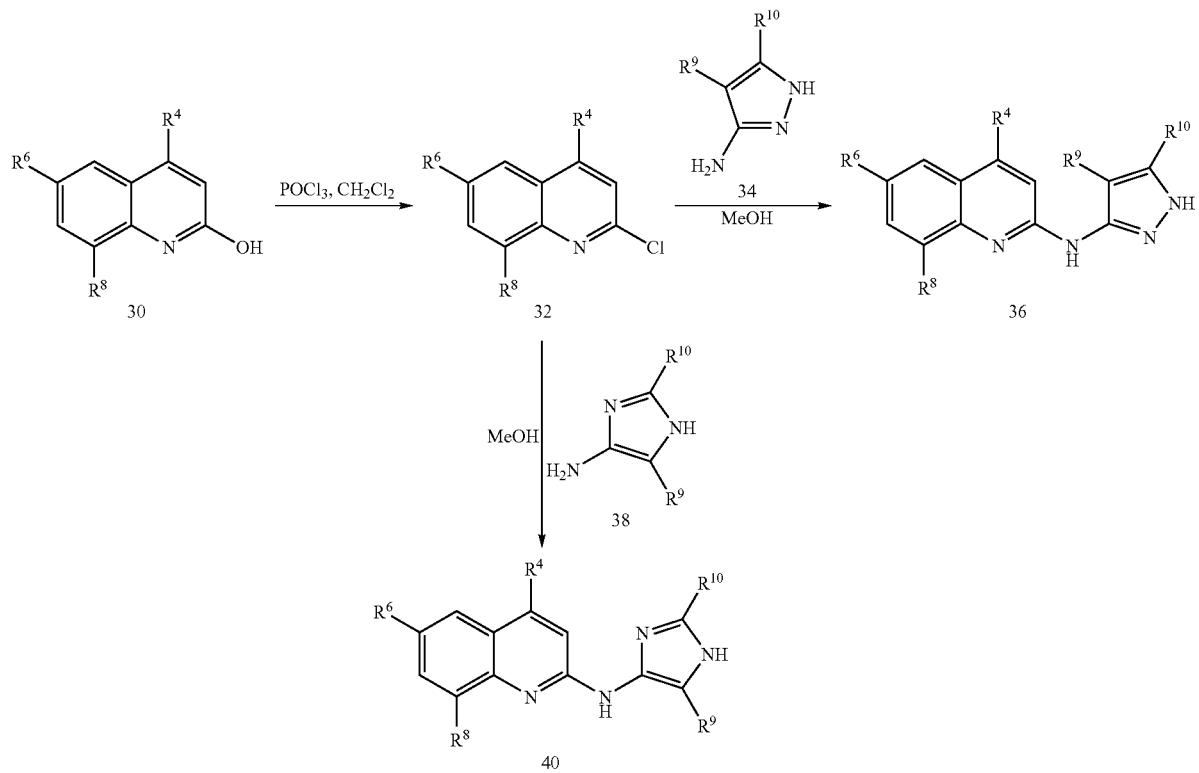

Scheme (I)

In Scheme (I), $R^4$, $R^6$, $R^8$, $R^9$ and $R^{10}$ are as defined for structural formulae (I)-(IV). According to Scheme (I), 2-hydroxyquinoline 30 can be converted to 2-chloro-quinoline 32 using standard techniques. 2-Chloro-quinoline 32 can be reacted with 1H-3-aminopyrazole 34 in methanol solvent at elevated temperature (e.g., 100° C.) or 1H-4-aminoimidazole 38 in methanol solvent in the presence of a catalytic amount of trifluoroacetic acid with microwaving to yield 2-substituted quinolines 36 and 40, respectively. Quinolines 30 and 32, as well as aminopyrazoles 34 and imidazoles 38, that include reactive functional groups can be masked with protecting groups, as is well know in the art. Guidance for selecting suitable protecting groups can be found in Greene and Wuts, Protective Groups in Organic Chemistry, 3rd Ed., 1999, John Wiley & Sons, NY and Harrison et al., Compendium of Synthetic Organic Methods, Vols. 1-8, 1971-1996, John Wiley & Sons, NY, the disclosures of which are incorporated herein by reference.

5.4 Inhibition of IgE Induced Mast Cell Degranulation

Active quinoline compounds inhibit the IgE signaling cascade that leads to, among other things, degranulation of mast and/or basophil cells. Both mast and basophil cells play a central role in allergen-induced disorders, including, for example, allergic rhinitis and asthma. Referring to FIG. 1, upon exposure allergens, which may be, among other things, pollen or parasites, allergen-specific IgE antibodies are synthesized by B-cells activated by IL-4 (or IL-13) and other messengers to switch to IgE class specific antibody synthesis. These allergen-specific IgEs bind to the high affinity Fcε receptor (FcεFR1 or IgE receptor) present on mast and/or basophil cells. Upon binding of antigen, the FcεR1-bound IgEs are cross-linked and the IgE receptor signal transduction pathway is activated, which leads to degranulation of the cells and consequent release and/or synthesis of a host of chemical mediators, including histamine, proteases (e.g., tryptase and chymase), lipid mediators such as leukotrienes (e.g., LTC4), platelet-activating factor (PAF) and prostaglandins (e.g., PGD2) and a series of cytokines, including TNF-α, IL-4, IL-13, IL-5, IL-6, IL-8, GMCSF, VEGF and TGF-β. The release and/or synthesis of these mediators from mast and/or basophil cells accounts for the early and late stage responses induced by allergens, and is directly linked to downstream events that lead to a sustained inflammatory state.

The molecular events in the IgE receptor signal transduction pathway that lead to release of preformed mediators via degranulation and release and/or synthesis of other chemical mediators are well-known and are illustrated in FIG. 2. Referring to FIG. 2, the IgE receptor (FcεR1) is a heterotetrameric receptor composed of an IgE-binding alpha-subunit, a beta subunit, and two gamma subunits. Cross-linking of IgE-bound IgE receptor by multivalent binding agents (including, for example IgE-specific allergens or anti-IgE antibody) induces the rapid association and activation of the Src-related kinase Lyn. Lyn phosphorylates immunoreceptor tyrosine-based activation motifs (ITAMS) on the intracellular beta and gamma subunits, which leads to the recruitment of additional Lyn to the beta subunit and Syk kinase to the gamma subunits. These receptor-associated kinases, which are activated by intra- and intermolecular phosphorylation, phosphorylate other components of the pathway such as the Btk kinase, LAT, and phospholipase C-gamma. Activated PLC-gamma initiates pathways that lead to protein kinase C activation and $Ca^{2+}$ mobilization, both of which are required for degranulation. FcεR1 cross-linking also activates the three major classes of mitogen activated protein (MAP) kinases, i.e. ERK1/2, JNK1/2, and p38. Activation of these pathways is important in the transcriptional regulation of proinflammatory mediators, such as TNF-α and IL-6, as well as the lipid mediator leukotriene C4 (LTC4).

The ability of the quinoline compounds described herein to inhibit the IgE receptor signaling cascade may be simply determined or confirmed in in vitro assays. Suitable assays are provided in the Examples section. In one typical assay, mast or basophils are first grown in the presence of IL-4, Stem Cell Factor (SCF), IL-6 and IgE to increase expression of the IgE receptor, exposed to a quinoline test compound and stimulated with anti-IgE antibodies (or, alternatively, an IgE-specific allergen). Following incubation, the amount of a chemical mediator or other chemical agent released and/or synthesized as a consequence of activating the IgE receptor signaling cascade may be quantified using standard techniques and compared to the amount of the mediator or agent released from control cells (i.e., cells that are stimulated but that are not exposed to test compound). The concentration of test compound that yields a 50% reduction in the quantity of the mediator or agent measured as compared to control cells is the $IC_{50}$ of the test compound. The origin of the mast or basophil cells used in the assay will depend, in part, on the desired use for the compounds and will be apparent to those of skill in the art. For example, if the compounds will be used to treat or prevent a particular disease in humans, a convenient source of mast or basophil cells is a human or other animal, which constitutes an accepted or known clinical model for the particular disease. Thus, depending upon the particular application, the mast or basophil cells may be derived from a wide variety of animal sources, ranging from, for example, lower mammals such as mice and rats, to dogs, sheep and other mammals commonly employed in clinical testing, to higher mammals such as monkeys, chimpanzees and apes, to humans. Specific examples of cells suitable for carrying out the in vitro assays include, but are not limited to, rodent or human basophil cells, rat basophil leukemia cell lines, primary mouse mast cells (such as bone marrow-derived mouse mast cells "BMMC") and primary human mast cells isolated from cord blood ("CHMC") or other tissues such as lung. Methods for isolating and culturing these cell types are well-known or are provided in the Examples section (see, e.g., Demo et al., 1999, Cytometry 36(4):340-348 and copending application Ser. No. 10/053,355, filed Nov. 8, 2001, the disclosures of which are incorporated herein by reference).

As will be recognized by skilled artisans, the mediator or agent quantified is not critical. The only requirement is that it be a mediator or agent released and/or synthesized as a consequence of initiating or activating the IgE receptor signaling cascade. Referring to FIG. 1, activation of this signaling cascade leads to numerous downstream events. For example, activation of the IgE receptor signal cascade leads to the immediate release (i.e., within 1-3 min. following receptor activation) of a variety of preformed chemical mediators and agents via degranulation. Thus, in one embodiment, the mediator or agent quantified may be specific to granules (i.e., present in granules but not in the cell cytoplasm generally). Examples of granule-specific mediators or agents that can be quantified to determine and/or confirm the activity of a quinoline compound include, but are not limited to, granule-specific enzymes such as hexosaminidase and tryptase and granule-specific components such as histamine and serotonin. Assays for quantifying such factors are well-known, and in many instances are commercially available. For example, tryptase and/or hexosaminidase release may be quantified by incubating the cells with cleavable substrates that fluoresce upon cleavage and quantifying the amount of fluorescence produced using conventional techniques. Such cleavable fluorogenic substrates are commercially available. For example, the fluorogenic substrates Z-Gly-Pro-Arg-AMC (Z=benzyloxycarbonyl; AMC=7-amino-4-methylcoumarin; BIOMOL Research Laboratories, Inc., Plymouth Meeting, Pa. 19462, Catalog No. P-142) and Z-Ala-Lys-Arg-AMC (Enzyme Systems Products, a division of ICN Biomedicals, Inc., Livermore, Calif. 94550, Catalog No. AMC-246) can be used to quantify the amount of tryptase released. The fluorogenic substrate 4-methylumbelliferyl-N-acetyl-β-D-glucosaminide (Sigma, St. Louis, Mo., Catalog #69585) can be used to quantify the amount of hexosaminidase released. Histamine release may be quantified using a commercially available enzyme-linked immunosorbent assay (ELISA) such as Immunotech histamine ELISA assay #IM2015 (Beckman-Coulter, Inc.). Specific methods of quantifying the release of tryptase, hexosaminidase and histamine are provided in the Examples section. Any of these assays may be used to determine or confirm the activity of the quinoline compounds described herein.

Referring again to FIG. 1, degranulation is only one of several responses initiated by the IgE receptor signaling cascade. In addition, activation of this signaling pathway leads to the de novo synthesis and release of cytokines and chemokines such as IL-4, IL-5, IL-6, TNF-α, IL-13 and MIP1-α), and release of lipid mediators such as leukotrienes (e.g., LTC4), platelet activating factor (PAF) and prostaglandins. Accordingly, the quinoline compounds may also be assessed for activity by quantifying the amount of one or more of these mediators released and/or synthesized by activated cells.

Unlike the granule-specific components discussed above, these "late stage" mediators are not released immediately following activation of the IgE receptor signaling cascade. Accordingly, when quantifying these late stage mediators, care should be taken to insure that the activated cell culture is incubated for a time sufficient to result in the synthesis (if necessary) and release of the mediator being quantified. Generally, PAF and lipid mediators such as leukotriene C4 are released 3-30 min. following IgE receptor activation. The cytokines and other late stage mediators are released approx. 4-8 hrs. following IgE receptor activation. Incubation times suitable for a specific mediator will be apparent to those of skill in the art. Specific guidance and assays are provided in the Examples section.

The amount of a particular late stage mediator released may be quantified using any standard technique. In one embodiment, the amount(s) may be quantified using ELISA assays. ELISA assay kits suitable for quantifying the amount of TNFα, IL-4, IL-5, IL-6 and/or IL-13 released are available from, for example, Biosource International, Inc., Camarillo, Calif. 93012 (see, e.g., Catalog Nos. KHC3011, KHC0042, KHC0052, KHC0061 and KHC0132). ELISA assay kits suitable for quantifying the amount of leukotriene C4 (LTC4) released from cells are available from Cayman Chemical Co., Ann Arbor, Mich. 48108 (see, e.g., Catalog No. 520211).

Typically, active quinoline compounds will exhibit $IC_{50}$s with respect to IgE-induced or IgE receptor-mediated degranulation and/or mediator release or synthesis of about 20 µM or lower, as measured in an in vitro assay, such as one of the in vitro assays described above or in the Examples section. Of course, skilled artisans will appreciate that compounds which exhibit lower $IC_{50}$s, for example on the order of 10 µM, 1 µM, 100 nM, 10 nM, 1 nM, or even lower, are particularly useful. Skilled artisans will appreciate that the various mediators discussed above may induce different adverse effects or exhibit different potencies with respect to the same adverse effect. For example, the lipid mediator LCT4 is a potent vasoconstrictor—it is approximately 1000-fold more potent at inducing vasoconstriction than histamine. As another example, in addition to mediating atopic or Type I hypersensitivity reactions, cytokines can also cause tissue remodeling and cell proliferation. Thus, although compounds that inhibit release and/or synthesis of any one of the previously discussed chemical mediators are useful, skilled artisans will appreciate that compounds which inhibit the release and/or synthesis of a plurality, or even all, of the previously described mediators find particular use, as such compounds are useful for ameliorating or avoiding altogether a plurality, or even all, of the adverse effects induced by the particular mediators. For example, compounds, which inhibit the release of all three types of mediators—granule-specific, lipid and cytokine—are useful for treating or preventing immediate Type I hypersensitivity reactions as well as the chronic symptoms associated therewith.

Quinoline compounds capable of inhibiting the release of more than one type of mediator (e.g., granule-specific or late stage) may be identified by determining the $IC_{50}$ with respect to a mediator representative of each class using the various in vitro assays described above (or other equivalent in vitro assays). Compounds which are capable of inhibiting the release of more than one mediator type will typically exhibit an $IC_{50}$ for each mediator type tested of less than about 20 µM. For example, a compound which exhibits an $IC_{50}$ of 1 µM with respect to histamine release ($IC_{50}^{histamine}$) and an $IC_{50}$ of 1 nM with respect to leukotriene LTC4 synthesis and/or release ($IC_{50}^{LTC4}$) inhibits both immediate (granule-specific) and late stage mediator release. As another specific example, a compound that exhibits an $IC_{50}^{tryptase}$ of 10 µM, an $IC_{50}^{LTC4}$ of 1 µM and an $IC_{50}^{IL-4}$ of 1 µM inhibits immediate (granule-specific), lipid and cytokine mediator release. Although the above specific examples utilize the $IC_{50}$s of one representative mediator of each class, skilled artisans will appreciate that the $IC_{50}$s of a plurality, or even all, mediators comprising one or more of the classes may be obtained. The quantity(ies) and identity(ies) of mediators for which $IC_{50}$ data should be ascertained for a particular compound and application will be apparent to those of skill in the art.

One particularly useful class of compounds includes those quinoline compounds that inhibit the release of immediate granule-specific mediators and late stage mediators with approximately equivalent $IC_{50}$s. By approximately equivalent is meant that the $IC_{50}$ for each mediator type are within about a 10-fold range of one another. Another particularly useful class of compounds includes those quinoline compounds that inhibit the release of immediate granule-specific mediators, lipid mediators and cytokine mediators with approximately equivalent $IC_{50}$s. In a specific embodiment, such compounds inhibit the release of the following mediators with approximately equivalent $IC_{50}$s: histamine, tryptase, hexosaminidase, IL-4, IL-5, IL-6, IL-13, TNFα and LTC4. Such compounds are particularly useful for, among other things, ameliorating or avoiding altogether both the early and late stage responses associated with atopic or immediate Type I hypersensitivity reactions.

Ideally, the ability to inhibit the release of all desired types of mediators will reside in a single compound. However, mixtures of compounds can also be identified that achieve the same result. For example, a first compound which inhibits the release of granule specific mediators may be used in combination with a second compound which inhibits the release and/or synthesis of cytokine mediators.

In addition to the IgE-induced (or IgE receptor-mediated) degranulation pathway discussed above, degranulation of mast and/or basophil cells can be induced by other agents. For example, ionomycin, a calcium ionophore that bypasses the early IgE receptor signal transduction machinery of the cell, directly induces a calcium flux that triggers degranulation. Referring again to FIG. 2, activated PLCγ initiates pathways that lead to, among other things, calcium ion mobilization and subsequent degranulation. As illustrated, this $Ca^{2+}$ mobilization is triggered late in the IgE receptor signal transduction pathway. As mentioned above, and as illustrated in FIG. 3, ionomycin directly induces $Ca^{2+}$ mobilization and a $Ca^{2+}$ flux that leads to degranulation. Other ionophores that induce degranulation in this manner include A23187. The ability of granulation-inducing ionophores such as ionomycin to bypass the early stages of the IgE receptor signaling cascade may be used as a counter screen to identify active compounds that specifically exert their degranulation-inhibitory activity by blocking or inhibiting the early IgE receptor signaling cascade that is initiated when the IgE receptor is cross-linked by antigen. Compounds which specifically inhibit such early IgE receptor mediated degranulation inhibit not only degranulation and subsequent rapid release of histamine, tryptase and other granule contents, but also inhibit the pro-inflammatory activation pathways causing the release of TNFα, IL-4, IL-13 and the lipid mediators such as LTC4. Thus, compounds which specifically inhibit such early IgE receptor-mediated degranulation block or inhibit not only acute atopic or Type I hypersensitivity reactions, but also late responses involving multiple inflammatory mediators.

Compounds that specifically inhibit early IgE receptor mediated mast and/or basophil degranulation are those compounds that inhibit IgE-induced degranulation (for example, have an $IC_{50}$ of less than about 20 µM with respect to the release of a granule-specific mediator or component as measured in an in vitro assay with cells stimulated with an IgE binding agent) but that do not appreciably inhibit ionophore-induced degranulation. In one embodiment, compounds are considered to not appreciably inhibit ionophore-induced degranulation if they exhibit an $IC_{50}$ of ionophore-induced degranulation of greater than about 20 µM, as measured in an in vitro assay. Of course, active compounds that exhibit even higher $IC_{50}$s of ionophore-induced degranulation, or that do not inhibit ionophore-induced degranulation at all, are particularly useful. In another embodiment, compounds are considered to not appreciably inhibit ionophore-induced degranulation if they exhibit a greater than 10-fold difference in their $IC_{50}$s of IgE-receptor-mediated degranulation and ionophore-induced degranulation, as measured in an in vitro assay. Assays suitable for determining the $IC_{50}$ of ionophore-induced degranulation include any of the previously-described degranulation assays, with the modification that the cells are stimulated or activated with a degranulation-inducing calcium ionophore such as ionomycin or A23187 (A.G. Scientific, San Diego, Calif.) instead of anti-IgE antibodies or an IgE-specific allergen. Specific assays for assessing the ability of a particular quinoline compound to inhibit ionophore-induced degranulation are provided in the Examples section.

As will be recognized by skilled artisans, compounds which exhibit a high degree of selectivity of IgE-induced degranulation find particular use, as such compounds selectively target the IgE receptor cascade and do not interfere with other degranulation mechanisms. Compounds which exhibit a high degree of selectivity are generally 10-fold or more selective for IgE-induced degranulation over ionophore-induced degranulation, such as ionomycin-induced degranulation.

5.5 Uses and Compositions

As previously discussed, the active quinoline compounds inhibit the IgE receptor signaling cascade leading to the release and/or synthesis of chemical mediators from mast and/or basophil cells, either via degranulation or other processes. As also discussed, many of the active compounds exert their inhibitory activity by acting early in the IgE receptor signal transduction pathway. As a consequence of these activities, the active compounds may be used in a variety of in vitro, in vivo and ex vivo contexts to regulate or inhibit the release of chemical mediators from mast and/or basophil cells. For example, in one embodiment, the compounds may be used as controls or standards in in vitro or in vivo screening assays to identify other compounds capable of inhibiting mast and/or basophil degranulation. In another embodiment, the active compounds may be used to regulate or inhibit the IgE receptor signaling cascade and/or IgE-induced mast and/or basophil degranulation as a therapeutic approach towards the treatment or prevention of diseases characterized by, caused by and/or associated with the release or synthesis of chemical mediators or IgE-induced mast and/or basophil degranulation. Such treatments may be administered to animals in veterinary contexts or to humans. Diseases that are characterized by, caused by or associated with such mediator release, synthesis or degranulation, and that can therefore be treated or prevented with the active compounds include, by way of example and not limitation, atopy or anaphylactic hypersensitivity or allergic reactions, allergies (e.g., allergic conjunctivitis, allergic rhinitis, atopic asthma, atopic dermatitis and food allergies), low grade scarring (e.g., of scleroderma, increased fibrosis, keloids, post-surgical scars, pulmonary fibrosis, vascular spasms, migraine, reperfusion injury and post myocardial infarction), diseases associated with tissue destruction (e.g., of COPD, rheumatoid arthritis, cardiobronchitis and post myocardial infarction), diseases associated with tissue inflammation (e.g., irritable bowel, spastic colon and inflammatory colon disease), inflammation, certain autoimmune diseases (e.g., lupus, rheumatoid arthritis, multiple sclerosis, etc.) and scarring.

When used to treat or prevent such diseases, the active compounds may be administered singly, as mixtures of one or more active compounds or in mixture or combination with other agents useful for treating such diseases and/or the symptoms associated with such diseases. The active compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, β-agonists, tryptase inhibitors and antihistamines, to name a few. The active compounds may be administered per se in the form of prodrugs or as pharmaceutical compositions, comprising an active compound or prodrug.

Pharmaceutical compositions comprising the active compounds (or prodrugs thereof) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically.

The active compound or prodrug may be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, baccal, systemic, nasal, injection, transdermal, rectal, vaginal, etc., or a form suitable for administration by inhalation or insufflation.

For topical administration, the active compound(s) or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH 5 to pH 7, with a pH of about pH 5.5 being typical.

For ocular administration, the active compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. No. 6,261,547; U.S. Pat. No. 6,197,934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851.

For prolonged delivery, the active compound(s) or prodrug(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Alternatively, other pharmaceutical delivery systems may be employed. Liposomes and emulsions are well-known examples of delivery vehicles that may be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

5.6 Effective Dosages

The active compound(s) or prodrug(s), or compositions thereof, will generally be used in an amount effective to achieve the intended result, for example in an amount effective to treat or prevent the particular disease being treated. The compound(s) may be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound may be administered to a patient at risk of developing one of the previously described diseases. For example, if it is unknown whether a patient is allergic to a particular drug, the compound may be administered prior to administration of the drug to avoid or ameliorate an allergic response to the drug. Alternatively, prophylactic administration may be applied to avoid the onset of symptoms in a patient diagnosed with the underlying disorder. For example, a compound may be administered to an allergy sufferer prior to expected exposure to the allergen. Compounds may also be administered prophylactically to healthy individuals who are repeatedly exposed to agents known to one of the above-described maladies to prevent the onset of the disorder. For example, a compound may be administered to a healthy individual who is repeatedly exposed to an allergen known to induce allergies, such as latex, in an effort to prevent the individual from developing an allergy. Alternatively, a compound may be administered to a patient suffering from asthma prior to partaking in activities which trigger asthma attacks to lessen the severity of, or avoid altogether, an asthmatic episode.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage for use in animals including humans may be formulated to achieve a circulating blood or serum concentration of active compound that is at or above an $IC_{50}$ of the particular compound as measured in as in vitro assay, such as the in vitro CHMC or BMMC and other in vitro assays described in the Examples section. Calculating dosages to achieve such circulating blood or serum concentrations taking into account the bioavailability of the particular compound is well within the capabilities of skilled artisans. For guidance, the reader is referred to Fingl & Woodbury, "General Principles," In: Goodman and Gilman's The Pharmaceutical Basis of Therapeutics, Chapter 1, pp. 1-46, latest edition, Pergamon Press, and the references cited therein.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, 1995, Allergy 50(21Suppl):6-9, discussion 34-38 and Tumas et al., 2001, J. Allergy Clin. Immunol. 107(6): 1025-1033. Suitable animal models of allergic rhinitis are described in Szelenyi et al., 2000, Arzneimittelforschung 50(11):1037-42; Kawaguchi et al., 1994, Clin. Exp. Allergy 24(3):238-244 and Sugimoto et al., 2000, Immunopharmacology 48(1):1-7. Suitable animal models of allergic conjunctivitis are described in Carreras et al., 1993, Br. J. Ophthalmol. 77(8):509-514; Saiga et al., 1992, Ophthalmic Res. 24(1):45-50; and Kunert et al., 2001, Invest. Ophthalmol. Vis. Sci. 42(11):2483-2489. Suitable animal models of systemic mastocytosis are described in O'Keefe et al., 1987, J. Vet. Intern. Med. 1(2):75-80 and Bean-Knudsen et al., 1989, Vet. Pathol. 26(1):90-92. Suitable animal models of hyper IgE syndrome are described in Claman et al., 1990, Clin. Immunol. Immunopathol. 56(1):46-53. Suitable animal models of B-cell lymphoma are described in Hough et al., 1998, Proc. Natl. Acad. Sci. USA 95:13853-13858 and Hakim et al., 1996, J. Immunol. 157(12):5503-5511. Suitable animal models of atopic disorders such as atopic dermatitis, atopic eczema and atopic asthma are described in Chan et al., 2001, J. Invest. Dermatol. 117(4):977-983 and Suto et al., 1999, Int. Arch. Allergy Immunol. 120(Suppl 1):70-75. Ordinarily skilled artisans can routinely adapt such information to determine dosages suitable for human administration. Additional suitable animal models are described in the Examples section.

Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) which are sufficient to maintain therapeutic or prophylactic effect. In cases of local administration or selective uptake, such as local topical administration, the effective local concentration of active compound(s) may not be related to plasma concentration. Skilled artisans will be able to optimize effective local dosages without undue experimentation.

The compound(s) may be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) effect is the therapeutic index. Compounds(s) that exhibit high therapeutic indices are preferred.

Exemplary embodiments of the various inventions having been described, the following examples are offered by way of illustration and not limitation.

6. EXAMPLES

6.1 Synthesis of Exemplary Quinoline Compounds

The various exemplary quinoline compounds illustrated in TABLE 1, supra, were synthesized as described in Scheme (I), supra. Conditions for the synthesis and isolation of representative compounds are provided below. Other quinoline compounds and prodrugs of such compounds can be prepared by routine modification of these methods.

6.1.1 2-(5-aminocarbonyl-1H-imidazol-4-ylamino)-8-chloroquinoline (Compound 5)

4-Aminoimidazole-5-carboxamide HCl salt (100 mg) and 2,8-dichloroquinoline (100 mg) were dissolved in methanol (5 mL). Catalytic amount of TFA was added. The reaction solution was microwaved at 160° C. for 4800 s. The reaction solution was evaporated and purified by flash column chromatography (CH2Cl2/MeOH=20:1) to give 8-chloro-2-(5-carboxamide-1H-imidazol-4-ylamino)quinoline as a white solid. 1H NMR (CDCl$_3$): δ 7.04 (d, J=8.7 Hz, 1H), 7.23 (t, J=8.1 Hz, 1H), 7.38 (s, 1H), 7.57 (d, J=8.1 Hz, 1H), 7.68 (d, J=7.5 Hz, 1H), 7.99 (d, J=9.3 Hz, 1H); LCMS: ret. time: 10.01 min.; purity: 100%; MS (m/e): 288.24 (M+H+).

The following compounds were synthesized by the method of Example 6.1.1

6.1.2 2-(5-chloro-1H-imidazol-4-ylamino)-8-hydroxyquinoline (Compound 21)

LCMS: ret. time: 12.38 min.; purity: 98.00%; MS (m/e): 217.16 (M-43).

6.1.3 2-(5-aminocarbonyl-1H-imidazol-4-ylamino)-4-methylquinoline (Compound 15)

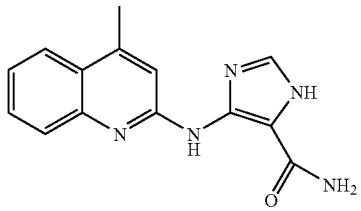

LCMS: ret. time: 9.82 min.; purity: 83.45%; MS (m/e): 268.27 (M+H+).

6.1.4 2-(5-aminocarbonyl-1H-imidazol-4-ylamino)quinoline (Compound 23)

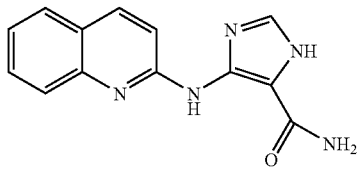

LCMS: ret. time: 8.96 min.; purity: 80.19%; MS (m/e): 254.27 (M+H+).

6.1.5 2-(5-aminocarbonyl-1H-imidazol-4-ylamino)-6-chloroquinoline (Compound 4)

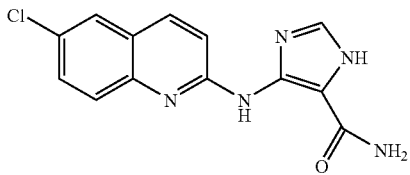

LCMS: ret. time: 9.62, 10.30 min.; purity: 92.16%; MS (m/e): 288.22 (M+H+).

6.1.6 2-(5-aminocarbonyl-1H-imidazol-4-ylamino)-4-methylaminocarbonylquinoline (Compound 18)

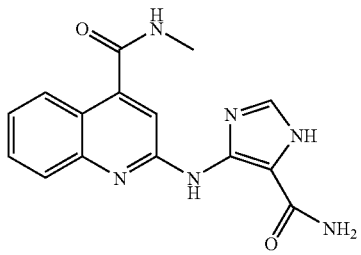

LCMS: ret. time: 6.82, 7.79 min.; purity: 90.22%; MS (m/e): 311.20 (M+H+).

6.1.7 2-(5-aminocarbonyl-1H-imidazol-4-ylamino)-4-(4-morpholinocarbonyl)quinoline (Compound 22)

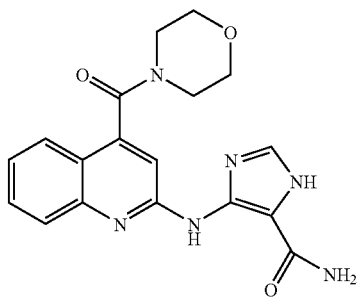

LCMS: ret. time: 7.74, 8.34 min.; purity: 94.09%; MS (m/e): 367.20 (M+H+).

6.1.8 2-(4-aminocarbonyl-1H-pyrazol-3-ylamino)-8-chloroquinoline (Compound 6)

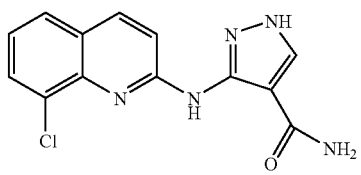

3-Amino-4-carboxamidepyrazole (100 mg) and 2,8-dichloroquinoline (50 mg) were dissolved in methanol (5 mL). The reaction solution was heated at 100° C. for 3 d. The reaction solution was evaporated. The residue was redissolved in methanol and ethyl acetate, sonicated and cooled downed. The precipitation was filtered off, washed with dichloromethane to give 8-chloro-2-(4-carboxamide-1H-pyrazol-3-ylamino)quinoline as a white solid. 1H NMR (DMSO-d6): δ 7.36 (br, 1H), 7.47 (t, 1H), 7.84 (br, 1H), 7.92 (m, 2H), 8.28 (s, 1H), 8.47 (d, J=9.0 Hz, 1H); LCMS: ret. time: 9.78 min.; purity: 95.89%; MS (m/e): 288.29 (M+H+).

The following additional compounds were synthesized by the method of Example 6.1.8

6.1.9 8-chloro-2-(3-phenyl-1H-pyrazol-5-ylamino)quinoline (Compound 7)

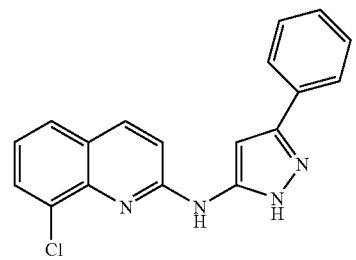

LCMS: ret. time: 10.48 min.; purity: 99.08%; MS (m/e): 321.14 (M+H+).

6.1.10 6-chloro-2-(3-phenyl-1H-pyrazol-5-ylamino)quinoline (Compound 1)

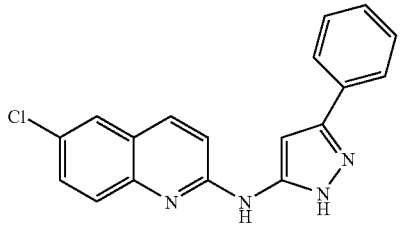

LCMS: ret. time: 10.22 min.; purity: 86.82%; MS (m/e): 321.10 (M+H+).

6.1.11 8-chloro-2-(3-thiophen-2-yl-1H-pyrazol-5-ylamino)quinoline (Compound 8)

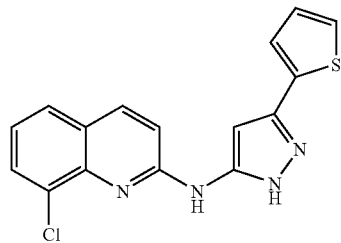

LCMS: ret. time: 10.98 min.; purity: 96.73%; MS (m/e): 327.09 (M+H+).

6.1.12 6-chloro-2-(3-thiophen-2-yl-1H-pyrazol-5-ylamino)quinoline (Compound 9)

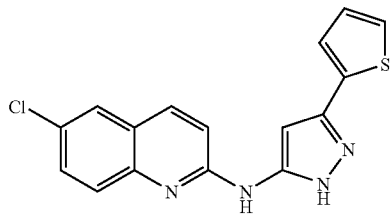

LCMS: ret. time: 10.48 min.; purity: 91.86%; MS (m/e): 327.06 (M+H+).

6.1.13 8-chloro-2-(1H-pyrazol-3-ylamino)quinoline (Compound 19)

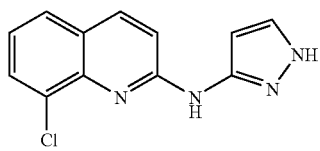

LCMS: ret. time: 6.97 min.; purity: 100%; MS (m/e): 245.11 (M+H+).

6.1.14 2-(5-tert-butyl-1H-pyrazol-3-ylamino)-8-chloroquinoline (Compound 13)

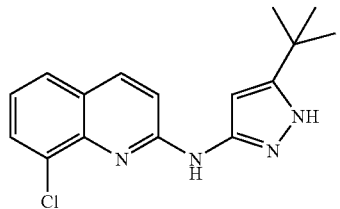

LCMS: ret. time: 10.05 min.; purity: 89.60%; MS (m/e): 301.17 (M+H+).

6.1.15 8-chloro-2-(4-cyano-1H-pyrazol-3-ylamino)quinoline (Compound 20)

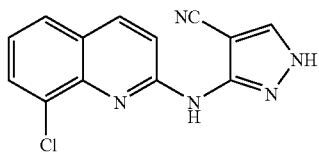

LCMS: ret. time: 13.57 min.; purity: 91.21%; MS (m/e): 270.27 (M+H+).

6.1.16 8-chloro-2-(4-ethoxycarbonyl-1H-pyrazol-3-ylamino)quinoline (Compound 17)

LCMS: ret. time: 14.01, 15.36 min.; purity: 98.04%; MS (m/e): 317.15 (M+H+).

6.1.17 8-chloro-2-(5-methyl-1H-pyrazol-3-ylamino)quinoline (Compound 12)

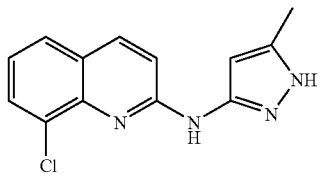

LCMS: ret. time: 9.08 min.; purity: 100%; MS (m/e): 259.30 (M+H+).

6.1.18 2-(4-bromo-5-phenyl-1H-pyrazol-3-ylamino)-8-chloroquinoline (Compound 2)

LCMS: ret. time: 16.16 min.; purity: 88.84%; MS (m/e): 401.07 (M+H+).

6.1.19 8-chloro-2-[5-(4-methoxyphenyl)-1H-pyrazol-3-ylamino]quinoline (Compound 10)

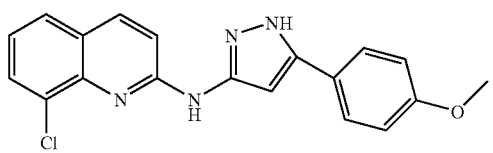

LCMS: ret. time: 12.07 min.; purity: 92.50%; MS (m/e): 351.27 (M+H+).

6.1.20 2-(4-aminocarbonyl-1H-pyrazol-3-ylamino)-6-chloroquinoline (Compound 16)

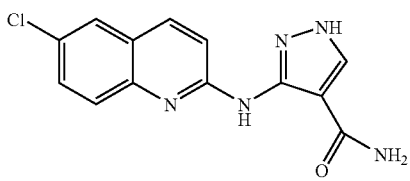

LCMS: ret. time: 9.44 min.; purity: 88.00%; MS (m/e): 288.28 (M+H+).

6.1.21 2-(4-bromo-5-phenyl-1H-pyrazol-3-ylamino)-6-chloroquinoline (Compound 3)

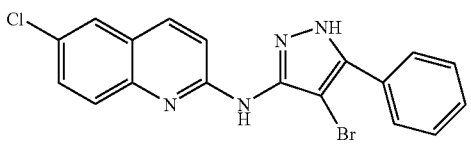

LCMS: ret. time: 14.68 min.; purity: 87.68%; MS (m/e): 401.07 (M+H+).

6.1.22 6-chloro-2-[5-(4-methoxyphenyl)-1H-pyrazol-3-ylamino]quinoline (Compound 11)

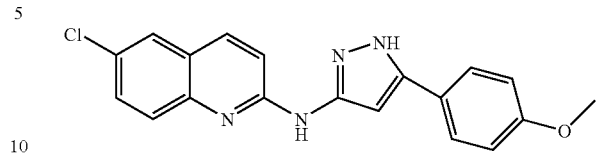

LCMS: ret. time: 11.88 min.; purity: 100%; MS (m/e): 351.27 (M+H+).

6.2 The Quinoline Compounds Inhibit IgE-Induced Degranulation in Cellular Assays The ability of representative quinoline compounds to inhibit IgE-induced degranulation was demonstrated in cellular assays with cultured human mast cells (CHMC) and can be measured by mouse bone marrow derived cells (BMMC). Inhibition of degranulation was measured at low density (and could also be measures at high cell density) by quantifying the release of the granule specific factor tryptase. Tryptase was quantified using a fluorogenic substrates as described in its respective examples. Histamine, TNFα, IL-6, IL-13 and LTC4 can be quantified, if desired, using the following commercial ELISA kits: histamine (Immunotech #2015, Beckman Coulter), TNFα (Biosource #KHC3011), IL-6 (Biosource #KMC0061), IL-13 (Biosource #KHC0132) and LTC4 (Cayman Chemical #520211). The protocols for various assays are provided below.

6.3 Culturing of Human Mast and Basophil Cells

Human mast and basophil cells were cultured from CD34-negative progenitor cells as described below (see also the methods described in copending U.S. application Ser. No. 10/053,355, filed Nov. 8, 2001, and WO 03/020896, the disclosures of which are incorporated herein by reference).

6.4 Preparation of STEMPRO-34 Complete Medium

To prepare STEMPRO-34 complete medium ("CM"), 250 mL STEMPRO-34TM serum free medium ("SFM"; GibcoBRL, Catalog No. 10640) was added to a filter flask. To this was added 13 mL STEMPRO-34 Nutrient Supplement ("NS"; GibcoBRL, Catalog No. 10641) (prepared as described in more detail, below). The NS container was rinsed with approximately 10 mL SFM and the rinse added to the filter flask. Following addition of 5 mL L-glutamine (200 mM; Mediatech, Catalog No. MT 25-005-CI and 5 mL 100× penicillin/streptomycin) ("pen-strep"; HyClone, Catalog No. SV30010), the volume was brought to 500 mL with SFM and the solution was filtered.

The most variable aspect of preparing the CM is the method by which the NS is thawed and mixed prior to addition to the SFM. The NS should be thawed in a 37° C. water bath and swirled, not vortexed or shaken, until it is completely in solution. While swirling, take note whether there are any lipids that are not yet in solution. If lipids are present and the NS is not uniform in appearance, return it to the water bath and repeat the swirling process until it is uniform in appearance. Sometimes this component goes into solution immediately, sometimes after a couple of swirling cycles, and sometimes not at all. If, after a couple of hours, the NS is still not in solution, discard it and thaw a fresh unit. NS that appears non-uniform after thaw should not be used.

6.4.1 Expansion of CD34+ Cells

A starting population of CD34-positive (CD34+) cells of relatively small number (1-5×106 cells) was expanded to a relatively large number of CD34-negative progenitor cells (about 2-4×109 cells) using the culture media and methods described below. The CD34+ cells (from a single donor) were obtained from Allcells (Berkeley, Calif.). Because there is a degree of variation in the quality and number of CD34+ cells that Allcells typically provides, the newly delivered cells were transferred to a 15 mL conical tube and brought up to 10 mL in CM prior to use.

On day 0, a cell count was performed on the viable (phase-bright) cells and the cells were spun at 1200 rpm to pellet. The cells were resuspended to a density of 275,000 cells/mL with CM containing 200 ng/mL recombinant human Stem Cell Factor ("SCF"; Peprotech, Catalog No. 300-07) and 20 ng/mL human flt-3 ligand (Peprotech, Catalog No. 300-19) ("CM/SCF/flt-3 medium"). On about day 4 or 5, the density of the culture was checked by performing a cell count and the culture was diluted to a density of 275,000 cells/mL with fresh CM/SCF/flt-3 medium. On about day 7, the culture was transferred to a sterile tube and a cell count was performed. The cells were spun at 1200 rpm and resuspended to a density of 275,000 cells/mL with fresh CM/SCF/flt-3 medium.

This cycle was repeated, starting from day 0, a total of 3-5 times over the expansion period.

When the culture is large and being maintained in multiple flasks and is to be resuspended, the contents of all of the flasks are combined into a single container prior to performing a cell count. This ensures that an accurate cell count is achieved and provides for a degree of uniformity of treatment for the entire population. Each flask is checked separately for contamination under the microscope prior to combining to prevent contamination of the entire population.

Between days 17-24, the culture can begin to go into decline (i.e., approximately 5-10% of the total number of cells die) and fail to expand as rapidly as before. The cells are then monitored on a daily basis during this time, as complete failure of the culture can take place in as little as 24 hours. Once the decline has begun, the cells are counted, spun down at 850 rpm for 15 minutes, and resuspended at a density of 350,000 cells/mL in CM/SCF/flt-3 medium to induce one or two more divisions out of the culture. The cells are monitored daily to avoid failure of the culture.

When greater than 15% cell death is evident in the progenitor cell culture and some debris is present in the culture, the CD34-negative progenitor cells are ready to be differentiated.

6.4.2 Differentiation of CD34-Negative Progenitor Cells into Mucosal Mast Cells A second phase is performed to convert the expanded CD34-negative progenitor cells into differentiated mucosal mast cells. These mucosal cultured human mast cells ("CHMC") are derived from CD34+ cells isolated from umbilical cord blood and treated to form a proliferated population of CD34-negative progenitor cells, as described above. To produce the CD34-negative progenitor cells, the resuspension cycle for the culture was the same as that described above, except that the culture was seeded at a density of 425,000 cells/mL and 15% additional media was added on about day four or five without performing a cell count. Also, the cytokine composition of the medium was modified such that it contained SCF (200 ng/mL) and recombinant human IL-6 (200 ng/mL; Peprotech, Catalog No. 200-06 reconstituted to 100 ug/mL in sterile 10 mM acetic acid) ("CM/SCF/IL-6 medium").

Phases I and II together span approximately 5 weeks. Some death and debris in the culture is evident during weeks 1-3 and there is a period during weeks 2-5 during which a small percentage of the culture is no longer in suspension, but is instead attached to the surface of the culture vessel.

As during Phase I, when the culture is to be resuspended on day seven of each cycle, the contents of all flasks are combined into a single container prior to performing a cell count to ensure uniformity of the entire population. Each flask is checked separately for contamination under the microscope prior to combining to prevent contamination of the entire population.

When the flasks are combined, approximately 75% of the volume is transferred to the communal container, leaving behind about 10 mL or so in the flask. The flask containing the remaining volume was rapped sharply and laterally to dislodge the attached cells. The rapping was repeated at a right angle to the first rap to completely dislodge the cells.

The flask was leaned at a 45 degree angle for a couple of minutes before the remaining volume was transferred to the counting vessel. The cells were spun at 950 rpm for 15 min prior to seeding at 35-50 mL per flask (at a density of 425,000 cells/mL).

6.4.3 Differentiation of CD34-Negative Progenitor Cells into Connective Tissue-Type Mast Cells A proliferated population of CD34-negative progenitor cells is prepared as above and treated to form a tryptase/chymase positive (connective tissue) phenotype. The methods are performed as described above for mucosal mast cells, but with the substitution of IL-4 for IL-6 in the culture medium. The cells obtained are typical of connective tissue mast cells.

6.4.4 Differentiation of CD34-Negative Progenitor Cells into Basophil Cells

A proliferated population of CD34-negative progenitor cells is prepared as described in Section 6.4.1, above, and used to form a proliferated population of basophil cells. The CD34-negative cells are treated as described for mucosal mast cells, but with the substitution of IL-3 (at 20-50 ng/mL) for IL-6 in the culture medium.

6.4.5 CHMC Low Cell Density IgE Activation: Tryptase and LTC4 Assays

To duplicate 96-well U-bottom plates (Costar 3799) add 65 ul of compound dilutions or control samples that have been prepared in MT [137 mM NaCl, 2.7 mM KCl, 1.8 mM $CaCl_2$, 1.0 mM $MgCl_2$, 5.6 mM Glucose, 20 mM Hepes (pH 7.4), 0.1% Bovine Serum Albumin, (Sigma A4503)] containing 2% MeOH and 1% DMSO. Pellet CHMC cells (980 rpm, 10 min) and resuspend in pre-warmed MT. Add 65 ul of cells to each 96-well plate. Depending on the degranulation activity for each particular CHMC donor, load 1000-1500 cells/well. Mix four times followed by a 1 hr incubation at 37° C. During the 1 hr incubation, prepare 6× anti-IgE solution [rabbit anti-human IgE (1 mg/ml, Bethyl Laboratories A80-109A) diluted 1:167 in MT buffer]. Stimulate cells by adding 25 ul of 6× anti-IgE solution to the appropriate plates. Add 25 ul MT to un-stimulated control wells. Mix twice following addition of the anti-IgE. Incubate at 37° C. for 30 minutes. During the 30 minute incubation, dilute the 20 mM tryptase substrate stock solution [(Z-Ala-Lys-Arg-AMC.2TFA; Enzyme Systems Products, #AMC-246)] 1:2000 in tryptase assay buffer [0.1 M Hepes (pH 7.5), 10% w/v Glycerol, 10 uM Heparin (Sigma H-4898) 0.01% $NaN_3$]. Spin plates at 1000 rpm for 10 min to pellet cells. Transfer 25 ul of supernatant to a 96-well black bottom plate and add 100 ul of freshly diluted tryptase substrate solution to each well. Incubate plates at room temperature for 30 min. Read the optical density of the plates at 355 nm/460 nm on a spectrophotometric plate reader.

Leukotriene C4 (LTC4) is quantified using an ELISA kit on appropriately diluted supernatant samples (determined empirically for each donor cell population so that the sample measurement falls within the standard curve) following the supplier's instructions.

6.4.6 CHMC High Cell Density IgE Activation: Degranulation (Tryptase, Histamine), Leukotriene (LTC4), and Cytokine (TNFalpha, IL-13) Assays Cultured human mast cells (CHMC) are sensitized for 5 days with IL-4 (20 ng/ml), SCF (200 ng/ml), IL-6 (200 ng/ml), and Human IgE (CP 1035K from Cortx Biochem, 100-500 ng/ml depending on generation) in CM medium. After sensitizing, cells are counted, pelleted (1000 rpm, 5-10 minutes), and resuspended at $1-2\times10^6$ cells/ml in MT buffer. Add 100 ul of cell suspension to each well and 100 ul of compound dilutions. The final vehicle concentration is 0.5% DMSO. Incubate at 37° C. (5% $CO_2$) for 1 hour. After 1 hour of compound treatment, stimulate cells with 6× anti-IgE. Mix wells with the cells and allow plates to incubate at 37° C. (5% $CO_2$) for one hour. After 1 hour incubation, pellet cells (10 minutes, 1000 rpm) and collect 200 ul per well of the supernatant, being careful not to disturb pellet. Place the supernatant plate on ice. During the 7-hour step (see below) perform tryptase assay on supernatant that has been diluted 1:500. Resuspend cell pellet in 240 ul of CM media containing 0.5% DMSO and corresponding concentration of compound. Incubate CHMC cells for 7 hours at 37° C. (5% $CO_2$). After incubation, pellet cells (1000 rpm, 10 minutes) and collect 225 ul per well and place in −80° C. until ready to perform ELISAS. ELISAS are performed on appropriately diluted samples (determined empirically for each donor cell population so that the sample measurement falls within the standard curve) following the supplier's instructions.

6.4.7 BMMC High Cell Density IgE Activation: Degranulation (Hexosaminidase, Histamine), Leukotriene (LTC4), and Cytokine (TNFalpha, IL-6) Assays

(a) Preparation of WEHI-Conditioned Medium

WEHI-conditioned medium is obtained by growing murine myelomonocytic WEHI-3B cells (American Type Culture Collection, Rockville, Md.) in Iscove's Modified Eagles Media (Mediatech, Hernandon, Va.) supplemented with 10% heat-inactivated fetal bovine serum (FBS; JRH Biosciences, Kansas City, Mo.), 50 μM 2-mercaptoethanol (Sigma, St. Louis, Mo.) and 100 IU/mL penicillin-streptomycin (Mediatech) in a humidified 37° C., 5% $CO_2$/95% air incubator. An initial cell suspension is seeded at 200,000 cells/mL and then split 1:4 every 3-4 days over a period of two weeks. Cell-free supernatants are harvested, aliquoted and stored at −80° C. until needed.

(b) Preparation of BMMC Medium

BMMC media consists of 20% WEHI-conditioned media, 10% heat-inactivated FBS (JHR Biosciences), 25 mM HEPES, pH7.4 (Sigma), 2 mM L-glutamine (Mediatech), 0.1 mM non-essential amino acids (Mediatech), 1 mM sodium pyruvate (Mediatech), 50 μM 2-mercaptoethanol (Sigma) and 100 IU/mL penicillin-streptomycin (Mediatech) in RPMI 1640 media (Mediatech). To prepare the BMMC Media, all components are added to a sterile IL filter unit and filtered through a 0.2 μm filter prior to use.

(c) Protocol

Bone marrow derived mast cells (BMMC) are sensitized overnight with murine SCF (20 ng/ml) and monoclonal anti-DNP (10 ng/ml, Clone SPE-7, Sigma # D-8406) in BMMC media at a cell density of $666\times10^3$ cells/ml. After sensitizing, cells are counted, pelleted (1000 rpm, 5-10 minutes), and resuspended at $1-3\times10^6$ cells/ml in MT buffer. Add 100 ul of cell suspension to each well and 100 ul of compound dilutions. The final vehicle concentration is 0.5% DMSO. Incubate at 37° C. (5% $CO_2$) for 1 hour. After 1 hour of compound treatment, stimulate cells with 6× stimulus (60 ng/ml DNP-BSA). Mix wells with the cells and allow plates to incubate at 37° C. (5% $CO_2$) for one hour. After 1 hour incubation, pellet cells (10 minutes, 1000 rpm) and collect 200 ul per well of the supernatant, being careful not to disturb pellet, and transfer to a clean tube or 96-well plate. Place the supernatant plate on ice. During the 4-5 hour step (see next) perform the hexosaminidase assay. Resuspend cell pellet in 240 ul WEI-conditioned media containing 0.5% DMSO and corresponding concentration of compound. Incubate BMMC cells for 4-5 hours at 37° C. (5% $CO_2$). After incubation, pellet cells (1000 rpm, 10 minutes) and collect 225 ul per well and place in −80° C. until ready to perform ELISAS. ELISAS can be performed on appropriately diluted samples (determined empirically for each donor cell population so that the sample measurement falls within the standard curve) following the supplier's instructions.

Hexosaminidase assay: In a solid black 96-well assay plate, add 50 uL hexosaminidase substrate (4-methylumbelliferyl-N-acetyl-β-D-glucosaminide; 2 mM) to each well. Add 50 uL of BMMC cell supernatant (see above) to the hexosaminidase substrate, place at 37° C. for 30 minutes and read the plate at 5, 10, 15, and 30 minutes on a spectrophotometer.

6.4.8 Basophil IgE or Dustmite Activation: Histamine Release Assay

The basophil activation assay is carried out using whole human peripheral blood from donors allergic to dust mites with the majority of the red blood cells removed by dextran sedimentation. Human peripheral blood is mixed 1:1 with 3% dextran T500 and RBCs are allowed to settle for 20-25 min. The upper fraction is diluted with 3 volumes of D-PBS and cells are spun down for 10 min at 1500 rpm, RT. Supernatant is aspirated and cells are washed in an equal volume MT-buffer. Finally, cells are resuspended in MT-buffer containing 0.5% DMSO in the original blood volume. 80 uL of cells are mixed with 20 uL compound in the presence of 0.5% DMSO, in triplicate, in a V-bottom 96-well tissue culture plate. A dose range of 8 compound concentrations can be tested resulting in a 10-point dose response curve including maximum (stimulated) and minimum (unstimulated) response. Cells are incubated with compound for 1 hour at 37° C., 5% $CO_2$ after which 20 uL of 6× stimulus [1 ug/mL anti-IgE (Bethyl Laboratories) 667 au/mL house dustmite (Antigen Laboratories)] is added. The cells are stimulated for 30 minutes at 37° C., 5% $CO_2$. The plate is spun for 10 min at 1500 rpm at room temperature and 80 uL of the supernatant is harvested for histamine content analysis using a histamine ELISA kit (for example, the kit supplied by Immunotech.) The ELISA can be performed according to supplier's instructions.

6.4.9 Results

The results of low density CHMC assays for release of tryptase (Section 6.2.2) are provided for examplary quinoline compounds in TABLE 1, supra. In TABLE 1, a value of "+" indicates an $IC_{50}$ of 20 μM or less; a value of "++" indicates an $IC_{50}$ of 10 μM or less; and a value of "+++" indicates an $IIC_{50}$ of 5 μM or less. Most compounds tested had IC50s of less than 5 μM, with many exhibiting $IC_{50}$s in the sub-micromolar range. Two compounds (Compounds 21 and 22 (illustrated in TABLE 1), exhibited $IC_{50}$s of greater than 20 μM, and were generally considered inactive in the assay (denoted in TABLE 1 by a value of "–").

6.5 The Quinoline Compounds Selectively Inhibit the Upstream IgE Receptor Cascade To confirm that the quinoline compounds exert their inhibitory activity by blocking or inhibiting the early IgE receptor signal transduction cascade, the representative compounds delineated in TABLE 1, supra, were tested in cellular assays for ionomycin-induced degranulation, as described below.

6.6 CHMC Low Cell Density Ionomycin Activation: Tryptase Assay

Assays for ionomycin-induced mast cell degranulation were carried out as described for the CHMC Low Density IgE Activation assays (Section 6.6.2, supra), with the exception that during the 1 hour incubation, 6× ionomycin solution [5 mM ionomycin (Sigma I-0634) in MeOH (stock) diluted 1:416.7 in MT buffer (2 μM final)] was prepared and cells were stimulated by adding 25 μl of the 6× ionomycin solution to the appropriate plates.

6.7 Basophil Ionomycin Activation: Histamine Release Assay

Assays for ionomycin-induced basophil cell degranulation can be carried out as described for the Basophil IgE or Dustmite Activation Assay (Section 6.2.5, supra), with the exception that following incubation with compound, cells are stimulated with 20 μl of 2 μM ionomycin.

6.7.1 Results

Of the compounds tested, the vast majority did not inhibit ionomycin-induced degranulation, confirming that these compounds did not selectively inhibit the later (or downstream) IgE receptor signal transduction cascade.

These results were confirmed for certain compounds by measuring anti-IgE-induced and ionomycin-induced calcium ion flux in CHMC cells.

6.8 Immediacy of the Inhibitory Effect of the Quinoline Compounds

To test the immediacy of their inhibitory effect, quinolines can be added simultaneously with anti-IgE antibody activator in the cellular assays described above. All compounds can be tested to determine whether they block IgE-induced degranulation of CHMC cells to the same extent as when the compounds are pre-incubated with CHMC cells for 10 or 30 min. prior to receptor cross-linking.

6.9 Kinetics of Pharmacological Activity In Vitro

Compounds can be tested in washout experiments. In the experiments, CHMC cells can be activated immediately with anti-IgE antibody in the presence of 1.25 μM compound (time zero), or the compound can be washed out followed by activation with anti-IgE antibody at 30, 60 or 120 min.

6.10 Toxicity: T- and B-Cells

The ability of the quinoline compounds to exert their inhibitory activity without being toxic to cells of the immune system can be demonstrated in cellular assays with B- and T-cells. The protocols for the assays are provided below.

6.11 Jurkat (T-Cell) Toxicity

Dilute Jurkat cells to 2×105 cells/ml in complete RPMI (10% heat-inactivated fetal bovine serum) media and incubate at 37° C., 5% $CO_2$ for 18 hours. Add 65 μl cells at 7.7×105 cells/ml to a 96-well V-bottom plate (TC-treated, Costar) containing 65 μl 2× compound (final vehicle concentration is 0.5% DMSO, 1.5% MeOH). Mix, incubate plates for 18-24 hr at 37° C., 5% $CO_2$. Toxicity can be assessed by flow cytometric analysis of cellular light scatter.

6.12 BJAB (B-Cell) Toxicity

The B-cell line BJAB is cultured in log phase in RPMI1640+10% heat-inactivated fetal bovine serum, 1× L-glutamine, 1× penicillin, 1× streptavidin and 1× beta-mercaptoethanol at 37° C., 5% $CO_2$. First, BJABs are harvested, spun and resuspended in culture medium to a concentration of 7.7×105 cells/mL. 65 μL Cells can be mixed with 65 μL compound, in duplicate, and in the presence of 0.1% DMSO in a V-bottomed 96-well tissue culture plate. Cells can be incubated with compound at various dilutions at 37° C., 5% $CO_2$. Toxicity can be assessed by flow cytometric analysis of cellular light scatter.

6.13 Toxicity: Cell Titer Glo Assay

Seed 50 μl cells (1×106/ml) into each well containing 50 μl compound. The final vehicle concentration should be 0.5% DMSO, 1.5% MeOH. Shake plates for 1 minute to mix cells and compound. Incubate plates at 37° C. (5% $CO_2$) for 18 hours. Next day, harvest 50 μl cells from each well, add to 50 μl Cell Titer Glo reagent (Invitrogen). Shake plates for 1 minute. Read on luminometer.

6.14 The Compounds Can be Effective for the Treatment of Allergies

The in vivo efficacy of the quinoline compounds towards allergies can be evaluated in the mouse model of passive cutaneous anaphylaxis (PCA). This model provides a direct measure of IgE-induced degranulation of tissue mast cells. In this model, IgE primed animals are exposed to an allergen challenge and the change in permeability of dermal vasculature that results from histamine release from mast cells is measured by change in the amount of dye leakage into surrounding tissue. Inhibition of mediator release by compounds that modulate mast cell degranulation is easily measured by extracting the dye from the tissue.

6.14.1 Study Protocol and Results

In the PCA assay mice are passively sensitized by intradermal injection with anti-dinitrophenol (DNP) IgE antibodies (Day −1). At predetermined times (5-60 minutes prior to challenge), animals are treated with the test agent (Day 0). The modulatory effect of the agent on cutaneous mast cell degranulation is measured following intravenous injection of DNP conjugated to human serum albumin (HSA-DNP), together with Evans blue dye. The resulting cross-linking of the IgE receptor and subsequent mast cell degranulation-induced increase in vascular permeability is determined by measuring the amount of dye extravasation into the tissue. Dye is extracted from the tissue by formamide, and the absorbance of this extract is read at 620 nm. The inhibitory effect of drug treatment is reported as the percent inhibition compared to vehicle treatment, that is, the percent reduction in A620.

Two compounds have been tested as positive controls: the histamine antagonist diphenhydramine and the serotonin antagonist cyproheptadine. Both mediators (histamine and serotonin) are released upon IgE-mediated degranulation from the mouse mast cell. This is in contrast to human mast cells, which do not contain any serotonin. Dose response curve with diphenhydramine shows an inhibition of the PCA response up to 86% with the highest dose (50 mg/kg, i.p., 30 minutes pretreatment time). This high dose however was not well tolerated by the animals. For this reason, cyproheptadine can be used as a positive control. Cyproheptadine inhibited the PCA response by 61%+/−4% (8 mg/kg, i.p., 30 minutes pretreatment time, n=23 experiments).

6.15 The Compounds Can be Effective in the Treatment of Asthma

The in vivo efficacy of the compounds towards the treatment of asthma can be evaluated in a sheep model of allergic asthma. In this model, sheep can be administered aerosols of test compound via an endotracheal tube, followed by an aerosol challenge with antigen extracted from the roundworm, *Ascaris suum*, to which the sheep are naturally allergic. Allergen challenge leads to direct bronchoconstriction [early asthmatic response (EAR), and late asthmatic response (LAR)], and a persistent non-specific airway hyperresponsiveness (AHR). These three characteristics are similar to those seen in human allergic asthmatics. The activity of the test agent can be determined by changes in the lung resistance (RL), which is calculated from measurements of transpulmonary pressure, flow, and respiratory volume. The historical control data obtained from the same sheep following saline treatment and allergen challenge show a sharp increase of RL during the EAR that persists for approximately 2-3 hours following antigen challenge. The LAR is a less pronounced increase in RL, which starts from 5-6 hours following antigen challenge and is resolved by 8 hours post-challenge. Twenty-four hours after the challenge a dose response to carbachol is measured to determine the AHR, which is expressed as the dose of carbachol required to increase RL by 400% over baseline. This measurement is referred to as the provocative concentration of carbachol that elicits a 400% increase in RL over baseline (PC400). The data can be compared to historical control data for the same individual when administered a saline control aerosol and challenged with *Ascaris suum*.

6.16 Toxicity and Pharmacokinetics

The non-toxicity of the quinolines can be demonstrated using standard animal models, as described below.

6.16.1 Mouse 7-Day Repeated Dose Subcutaneous Administration Tolerance Study In this study, female BALB/c® mice can be treated by subcutaneous administration with either vehicle or test article formulation once daily for 7 days to determine the subcutaneous administration tolerability of a particular compound. The study consists of four toxicology groups as follows: mice in two separate drug-treated groups (of nine mice each) can be administered 30 mg/ml of a compound in a CMC suspension (50 mM phosphate buffer, pH7, with 0.1% (w/v) carboxymethyl cellulose) or a 67% PEG 400 solution (67% PEG 400/33% 50 mM citrate) at doses of 200 mg/kg/day and mice in two separate vehicle control groups (of six mice each) receive either 0.9% sodium chloride or 67% PEG 400 solution. The administered dose volume should be 6.7 ml/kg/day for all four groups of mice. Six mice in each of the drug-treated groups serve as toxicokinetic satellite animals (3 per group per timepoint) for toxicokinetic evaluation of parent and major metabolite (MM) levels at 24 hours after the first and seventh dose. Skin from the dose site can be collected and evaluated for microscopic changes.

6.16.2 Mouse 14-Day Repeated Dose Oral Toxicology Study

In this dose-ranging toxicology and toxicokinetics study, BALB/c mice can be treated by oral gavage with either vehicle only or test article formulation once daily for 14 days. The study consists of four toxicology groups of five mice per sex and four toxicokinetic satellite groups receiving the same treatment regimen in parallel. Vehicle control mice receive either 6.7 ml/kg/day or 16.7 ml/kg/day of a 67% PEG 400, 33% 50 mM citrate (v/v) formulation. Animals that can be treated with a test article receive either a low dose of 200 mg/kg/day (6.7 ml/kg/day) or a high dose of 500 mg/kg/day (16.7 ml/kg/day) of the test compound, using a 30 mg/ml solution.

6.16.3 Rat 14-Day Repeated Dose Toxicity Study

In this dose-ranging toxicology and toxicokinetics study, Sprague Dawley rats can be treated by oral gavage with either vehicle only or test article formulation once daily for 14 days. The study consists of four toxicology groups of five rats per sex and two toxicokinetics satellite groups. Five rats per sex received either 6.7 ml/kg/day (low volume control) or 16.7 ml/kg/day (high volume control), of a 67% PEG 400 33% 50 mM citrate (v/v) vehicle formulation. Five male rats can receive the low dose of 200 mg/kg/day of test compound (6.7 ml/kg), and five rats per sex can receive the high dose of 500 mg/kg/day of test compound (16.7 ml/kg/day) using a 30 mg/ml solution.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

All literature and patent references cited throughout the application are incorporated by reference into the application for all purposes.

What is claimed is:

1. A compound according to any one of structural formulae (I)-(IV):

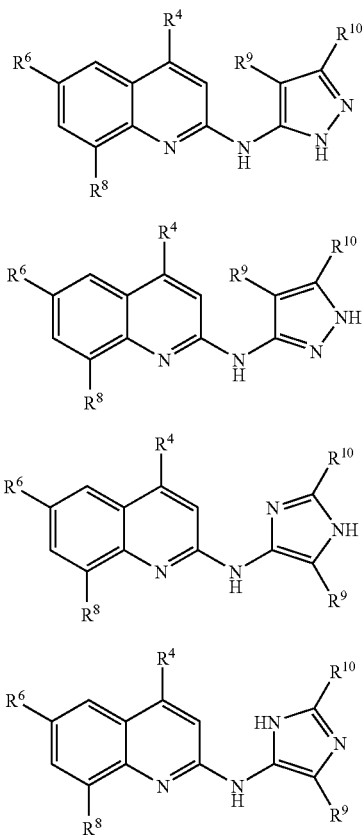

and salts and N-oxides thereof, wherein:
$R^4$ is selected from hydrogen, (C1-C6) alkyl, and —C(O)NR$^b$R$^b$;
$R^6$ is selected from hydrogen and halo;
$R^8$ is selected from hydrogen and halo;
$R^9$ is selected from hydrogen, halo, cyano, —C(O)OR$^b$, and —C(O)NR$^b$R$^b$;
$R^{10}$ is selected from hydrogen, (C1-C6) alkyl, branched (C1-C6) alkyl, phenyl, para-(C1-C6)alkoxyphenyl, para-methoxyphenyl, 5-membered heteroaryl, and thienyl; and
each R$^b$ is, independently of the others, selected from hydrogen and (C1-C6) alkyl,
wherein alkyl refers to a saturated or unsaturated branched, straight chain or cyclic monovalent radical that is derived by the removal of one hydrogen atom from a single carbon of a parent alkane, alkene, or alkyne;
with the proviso that at least one of $R^4$, $R^6$ and $R^8$ is other than hydrogen.

2. The compound of claim 1 in which each R$^b$ is, independently of the others, selected from hydrogen and methyl.

3. The compound of claim 1 in which $R^4$ is hydrogen, one of $R^6$ or $R^8$ is chloro and the other one of $R^6$ or $R^8$ is hydrogen.

4. The compound of claim 1 in which $R^4$ is methyl or —C(O)NHMe and $R^6$ $R^8$ are each hydrogen.

5. The compound of claim 1 in which $R^9$ is hydrogen and $R^{10}$ is other than hydrogen.

6. The compound of claim 5 in which $R^{10}$ is selected from phenyl, para-methoxyphenyl and thien-2-yl.

7. The compound of claim 1 in which $R^{10}$ is hydrogen and $R^9$ is other than hydrogen.

8. The compound of claim 7 in which $R^9$ is selected from —C(O)NH$_2$ and —C(O)OR$^b$, where R$^b$ is (C1-C4) alkyl.

9. The compound of claim 1 in which $R^9$ and $R^{10}$ are each other than hydrogen.

10. The compound of claim 1 in which $R^9$ is bromo and $R^{10}$ is phenyl.

11. The compound of claim 1 in which $R^9$ and $R^{10}$ are each hydrogen.

12. The compound of claim 1 in which $R^4$, $R^6$, $R^8$, $R^9$ and $R^{10}$ are selected from any combination of substituents delineated in TABLE 1.

13. The compound of claim 1 that is selected from any compound delineated in TABLE 1, or a salt, or N-oxide thereof.

14. A pharmaceutical composition comprising a compound according to claim 1 and a pharmaceutically acceptable carrier, diluent and/or excipient.

15. The composition of claim 14 in which the compound is in the form of a pharmaceutically acceptable salt.

16. A method of inhibiting degranulation of a mast or basophil cell, comprising contacting the mast or basophil cell with an amount of a compound according to claim 1 effective to inhibit degranulation.

17. The method of claim 16 in which the mast or basophil cell is a human mast or basophil cell.

18. A method of inhibiting degranulation of a mast or basophil cell, comprising contacting the mast or basophil cell with an amount of a composition according to claim 14 effective to inhibit degranulation.

19. The method of claim 18 in which the mast or basophil cell is a human mast or basophil cell.

* * * * *